United States Patent
Calomeni et al.

(10) Patent No.: US 10,779,940 B2
(45) Date of Patent: Sep. 22, 2020

(54) MEDICAL DEVICE HANDLE

(71) Applicant: BOSTON SCIENTIFIC SCIMED INC., Maple Grove, MN (US)

(72) Inventors: Michael P. Calomeni, San Jose, CA (US); Crissly Valdez Crisostomo, Folsom, CA (US); Randy S. Gamarra, Santa Clara, CA (US); Takashi H. Ino, San Jose, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 724 days.

(21) Appl. No.: 15/244,389

(22) Filed: Aug. 23, 2016

(65) Prior Publication Data
US 2017/0065406 A1 Mar. 9, 2017

Related U.S. Application Data

(60) Provisional application No. 62/213,931, filed on Sep. 3, 2015.

(51) Int. Cl.
| | | |
|---|---|---|
| *A61F 2/24* | (2006.01) | |
| *A61F 2/966* | (2013.01) | |
| *A61F 2/95* | (2013.01) | |

(52) U.S. Cl.
CPC .......... *A61F 2/243* (2013.01); *A61F 2/2436* (2013.01); *A61F 2/966* (2013.01); *A61F 2/9517* (2020.05); *A61F 2002/9665* (2013.01)

(58) Field of Classification Search
CPC .......... A62F 2/24; A62F 2/2427; A62F 2/243; A62F 2/2436; A62F 2/2466; A62F 2/95;
(Continued)

(56) References Cited

U.S. PATENT DOCUMENTS

| | | |
|---|---|---|
| 3,027,637 A | 4/1962 | Seiler |
| 3,241,259 A | 3/1966 | McBride |
| | (Continued) | |

FOREIGN PATENT DOCUMENTS

| | | |
|---|---|---|
| CN | 1338951 A | 3/2002 |
| EP | 0512725 A1 | 11/1992 |
| | (Continued) | |

OTHER PUBLICATIONS

Definition of slot, Merriam-webster dictionary, https://www.merriam-webster.com/dictionary/slot, accessed Oct. 18, 2019 (Year: 2009).*

(Continued)

*Primary Examiner* — Wade Miles
*Assistant Examiner* — Mikail A Mannan
(74) *Attorney, Agent, or Firm* — Seager, Tufte & Wickhem LLP

(57) ABSTRACT

A medical device handle for percutaneous delivery of a medical device implant may include an elongated handle housing having a proximal end, a distal end, and a longitudinal axis extending from the proximal end to the distal end; a rotatable collar disposed about the proximal end of the handle housing; and a rotatable control knob disposed about a proximal portion of the rotatable collar. The rotatable collar may include a first internally-facing longitudinal slot extending less than a full length of the rotatable collar and terminating proximally at a distally-facing wall of an internally-facing circumferentially-oriented slot. The rotatable control knob may be configured to actuate the medical device implant between a delivery configuration, a deployed configuration, and a released configuration.

15 Claims, 24 Drawing Sheets

(58) Field of Classification Search
CPC .. A62F 2/962; A62F 2/966; A61F 2002/9505; A61F 2002/9517; A61F 2002/9665
See application file for complete search history.

(56) References Cited

U.S. PATENT DOCUMENTS

| | | | |
|---|---|---|---|
| 3,334,629 A | 8/1967 | Cohn | |
| 3,409,013 A | 11/1968 | Berry | |
| 3,540,431 A | 11/1970 | Mobin-Uddin | |
| 3,628,535 A | 12/1971 | Ostrowsky et al. | |
| 3,642,004 A | 2/1972 | Osthagen et al. | |
| 3,657,744 A | 4/1972 | Ersek | |
| 3,671,979 A | 6/1972 | Moulopoulos | |
| 3,795,246 A | 3/1974 | Sturgeon | |
| 3,839,741 A | 10/1974 | Haller | |
| 3,868,956 A | 3/1975 | Alfidi et al. | |
| 3,874,388 A | 4/1975 | King et al. | |
| 4,056,854 A | 11/1977 | Boretos et al. | |
| 4,106,129 A | 8/1978 | Carpentier et al. | |
| 4,233,690 A | 11/1980 | Akins | |
| 4,291,420 A | 9/1981 | Reul | |
| 4,326,306 A | 4/1982 | Poler | |
| 4,423,809 A | 1/1984 | Mazzocco | |
| 4,425,908 A | 1/1984 | Simon | |
| 4,501,030 A | 2/1985 | Lane | |
| 4,580,568 A | 4/1986 | Gianturco | |
| 4,602,911 A | 7/1986 | Ahmadi et al. | |
| 4,610,688 A | 9/1986 | Silvestrini et al. | |
| 4,617,932 A | 10/1986 | Kornberg | |
| 4,647,283 A | 3/1987 | Carpentier et al. | |
| 4,648,881 A | 3/1987 | Carpentier et al. | |
| 4,655,218 A | 4/1987 | Kulik et al. | |
| 4,655,771 A | 4/1987 | Wallsten | |
| 4,662,885 A | 5/1987 | DiPisa, Jr. | |
| 4,665,906 A | 5/1987 | Jervis | |
| 4,710,192 A | 12/1987 | Liotta et al. | |
| 4,733,665 A | 3/1988 | Palmaz | |
| 4,755,181 A | 7/1988 | Igoe | |
| 4,773,420 A | 9/1988 | Green | |
| 4,796,629 A | 1/1989 | Grayzel | |
| 4,819,751 A | 4/1989 | Shimada et al. | |
| 4,834,755 A | 5/1989 | Silvestrini et al. | |
| 4,856,516 A | 8/1989 | Hillstead | |
| 4,865,600 A | 9/1989 | Carpentier et al. | |
| 4,872,874 A | 10/1989 | Taheri | |
| 4,909,252 A | 3/1990 | Goldberger | |
| 4,917,102 A | 4/1990 | Miller et al. | |
| 4,954,126 A | 9/1990 | Wallsten | |
| 4,986,830 A | 1/1991 | Owens et al. | |
| 4,994,077 A | 2/1991 | Dobben | |
| 5,002,556 A | 3/1991 | Ishida et al. | |
| 5,002,559 A | 3/1991 | Tower | |
| 5,064,435 A | 11/1991 | Porter | |
| 5,161,547 A | 11/1992 | Tower | |
| 5,163,953 A | 11/1992 | Vince | |
| 5,209,741 A | 5/1993 | Spaeth | |
| 5,211,086 A | 5/1993 | Shu | |
| 5,217,483 A | 6/1993 | Tower | |
| 5,258,042 A | 11/1993 | Mehta | |
| 5,332,402 A | 7/1994 | Teitelbaum | |
| 5,336,258 A | 8/1994 | Quintero et al. | |
| 5,350,398 A | 9/1994 | Pavcnik et al. | |
| 5,370,685 A | 12/1994 | Stevens | |
| 5,389,106 A | 2/1995 | Tower | |
| 5,397,351 A | 3/1995 | Pavcnik et al. | |
| 5,411,552 A | 5/1995 | Andersen et al. | |
| 5,425,762 A | 6/1995 | Muller | |
| 5,431,676 A | 7/1995 | Dubrul et al. | |
| 5,443,495 A | 8/1995 | Buscemi et al. | |
| 5,443,499 A | 8/1995 | Schmitt | |
| 5,476,506 A | 12/1995 | Lunn | |
| 5,476,510 A | 12/1995 | Eberhardt et al. | |
| 5,480,423 A | 1/1996 | Ravenscroft et al. | |
| 5,507,767 A | 4/1996 | Maeda et al. | |
| 5,534,007 A | 7/1996 | St. Germain et al. | |
| 5,545,133 A | 8/1996 | Burns et al. | |
| 5,545,211 A | 8/1996 | An et al. | |
| 5,549,665 A | 8/1996 | Vesely et al. | |
| 5,554,185 A | 9/1996 | Block et al. | |
| 5,571,215 A | 11/1996 | Sterman et al. | |
| 5,575,818 A | 11/1996 | Pinchuk | |
| 5,645,559 A | 7/1997 | Hachtman et al. | |
| 5,662,671 A | 9/1997 | Barbut et al. | |
| 5,667,523 A | 9/1997 | Bynon et al. | |
| 5,674,277 A | 10/1997 | Freitag | |
| 5,693,083 A | 12/1997 | Baker et al. | |
| 5,695,498 A | 12/1997 | Tower | |
| 5,713,953 A | 2/1998 | Vallana et al. | |
| 5,716,370 A | 2/1998 | Williamson, IV et al. | |
| 5,720,391 A | 2/1998 | Dohm et al. | |
| 5,733,325 A | 3/1998 | Robinson et al. | |
| 5,735,842 A | 4/1998 | Krueger et al. | |
| 5,769,812 A | 6/1998 | Stevens et al. | |
| 5,800,456 A | 9/1998 | Maeda et al. | |
| 5,807,405 A | 9/1998 | Vanney et al. | |
| 5,817,126 A | 10/1998 | Imran | |
| 5,824,041 A | 10/1998 | Lenker et al. | |
| 5,824,043 A | 10/1998 | Cottone, Jr. | |
| 5,824,053 A | 10/1998 | Khosravi et al. | |
| 5,824,055 A | 10/1998 | Spiridigliozzi et al. | |
| 5,824,056 A | 10/1998 | Rosenberg | |
| 5,824,064 A | 10/1998 | Taheri | |
| 5,843,158 A | 12/1998 | Lenker et al. | |
| 5,848,440 A | 12/1998 | Pajarola | |
| 5,855,597 A | 1/1999 | Jayaraman | |
| 5,855,601 A | 1/1999 | Bessler et al. | |
| 5,860,966 A | 1/1999 | Tower | |
| 5,861,024 A | 1/1999 | Rashidi | |
| 5,861,028 A | 1/1999 | Angell | |
| 5,868,783 A | 2/1999 | Tower | |
| 5,876,448 A | 3/1999 | Thompson et al. | |
| 5,885,228 A | 3/1999 | Rosenman et al. | |
| 5,888,201 A | 3/1999 | Stinson et al. | |
| 5,891,191 A | 4/1999 | Stinson | |
| 5,895,399 A | 4/1999 | Barbut et al. | |
| 5,907,893 A | 6/1999 | Zadno-Azizi et al. | |
| 5,910,154 A | 6/1999 | Tsugita et al. | |
| 5,911,734 A | 6/1999 | Tsugita et al. | |
| 5,925,063 A | 7/1999 | Khosravi | |
| 5,944,739 A | 8/1999 | Amplatz et al. | |
| 5,954,766 A | 9/1999 | Zadno-Azizi et al. | |
| 5,957,949 A | 9/1999 | Leonhardt et al. | |
| 5,968,070 A | 10/1999 | Bley et al. | |
| 5,984,957 A | 11/1999 | Laptewicz, Jr. et al. | |
| 5,984,959 A | 11/1999 | Robertson et al. | |
| 5,993,469 A | 11/1999 | McKenzie et al. | |
| 5,997,557 A | 12/1999 | Barbut et al. | |
| 6,010,522 A | 1/2000 | Barbut et al. | |
| 6,022,370 A | 2/2000 | Tower | |
| 6,027,520 A | 2/2000 | Tsugita et al. | |
| 6,027,525 A | 2/2000 | Suh et al. | |
| 6,042,598 A | 3/2000 | Tsugita et al. | |
| 6,042,607 A | 3/2000 | Williamson, IV et al. | |
| 6,093,203 A | 7/2000 | Uflacker | |
| 6,123,723 A | 9/2000 | Konya et al. | |
| 6,142,987 A | 11/2000 | Tsugita | |
| 6,162,245 A | 12/2000 | Jayaraman | |
| 6,165,200 A | 12/2000 | Tsugita et al. | |
| 6,165,209 A | 12/2000 | Patterson et al. | |
| 6,168,579 B1 | 1/2001 | Tsugita | |
| 6,171,327 B1 | 1/2001 | Daniel et al. | |
| 6,179,859 B1 | 1/2001 | Bates | |
| 6,187,016 B1 | 2/2001 | Hedges et al. | |
| 6,197,053 B1 | 3/2001 | Cosgrove et al. | |
| 6,200,336 B1 | 3/2001 | Pavcnik et al. | |
| 6,214,036 B1 | 4/2001 | Letendre et al. | |
| 6,221,006 B1 | 4/2001 | Dubrul et al. | |
| 6,221,091 B1 | 4/2001 | Khosravi | |
| 6,221,096 B1 | 4/2001 | Aiba et al. | |
| 6,231,544 B1 | 5/2001 | Tsugita et al. | |
| 6,231,551 B1 | 5/2001 | Barbut | |
| 6,241,757 B1 | 6/2001 | An et al. | |
| 6,245,102 B1 | 6/2001 | Jayaraman | |
| 6,251,135 B1 | 6/2001 | Stinson et al. | |

(56) References Cited

U.S. PATENT DOCUMENTS

| | | |
|---|---|---|
| 6,258,114 B1 | 7/2001 | Konya et al. |
| 6,258,115 B1 | 7/2001 | Dubrul |
| 6,258,120 B1 | 7/2001 | McKenzie et al. |
| 6,264,647 B1 | 7/2001 | Lechot |
| 6,267,783 B1 | 7/2001 | Letendre et al. |
| 6,270,513 B1 | 8/2001 | Tsugita et al. |
| 6,277,555 B1 | 8/2001 | Duran et al. |
| 6,309,417 B1 | 10/2001 | Spence et al. |
| 6,319,281 B1 | 11/2001 | Patel |
| 6,327,772 B1 | 12/2001 | Zadno-Azizi et al. |
| 6,336,934 B1 | 1/2002 | Gilson et al. |
| 6,336,937 B1 | 1/2002 | Vonesh et al. |
| 6,338,735 B1 | 1/2002 | Stevens |
| 6,348,063 B1 | 2/2002 | Yassour et al. |
| 6,352,708 B1 | 3/2002 | Duran et al. |
| 6,361,545 B1 | 3/2002 | Macoviak et al. |
| 6,371,970 B1 | 4/2002 | Khosravi et al. |
| 6,371,983 B1 | 4/2002 | Lane |
| 6,379,383 B1 | 4/2002 | Palmaz et al. |
| 6,398,807 B1 | 6/2002 | Chouinard et al. |
| 6,409,750 B1 | 6/2002 | Hyodoh et al. |
| 6,416,510 B1 | 7/2002 | Altman et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,468,303 B1 | 10/2002 | Amplatz et al. |
| 6,475,239 B1 | 11/2002 | Campbell et al. |
| 6,482,228 B1 | 11/2002 | Norred |
| 6,485,502 B2 | 11/2002 | Don Michael et al. |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,537,297 B2 | 3/2003 | Tsugita et al. |
| 6,540,768 B1 | 4/2003 | Diaz et al. |
| 6,562,058 B2 | 5/2003 | Seguin et al. |
| 6,592,546 B1 | 7/2003 | Barbut et al. |
| 6,592,614 B2 | 7/2003 | Lenker et al. |
| 6,610,077 B1 | 8/2003 | Hancock et al. |
| 6,616,682 B2 | 9/2003 | Joergensen et al. |
| 6,622,604 B1 | 9/2003 | Chouinard et al. |
| 6,623,518 B2 | 9/2003 | Thompson et al. |
| 6,626,892 B1 | 9/2003 | Mayer |
| 6,632,243 B1 | 10/2003 | Zadno-Azizi et al. |
| 6,635,068 B1 | 10/2003 | Dubrul et al. |
| 6,635,079 B2 | 10/2003 | Unsworth et al. |
| 6,652,571 B1 | 11/2003 | White et al. |
| 6,652,578 B2 | 11/2003 | Bailey et al. |
| 6,663,588 B2 | 12/2003 | Dubois et al. |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,668 B2 | 1/2004 | Mercereau et al. |
| 6,676,692 B2 | 1/2004 | Rabkin et al. |
| 6,676,698 B2 | 1/2004 | McGuckin, Jr. et al. |
| 6,682,543 B2 | 1/2004 | Barbut et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,695,864 B2 | 2/2004 | Macoviak et al. |
| 6,695,865 B2 | 2/2004 | Boyle et al. |
| 6,702,851 B1 | 3/2004 | Chinn et al. |
| 6,712,842 B1 | 3/2004 | Gifford, III et al. |
| 6,712,843 B2 | 3/2004 | Elliott |
| 6,714,842 B1 | 3/2004 | Ito |
| 6,719,789 B2 | 4/2004 | Cox |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,746,412 B1 | 6/2004 | Hill et al. |
| 6,752,828 B2 | 6/2004 | Thornton |
| 6,758,855 B2 | 7/2004 | Fulton, III et al. |
| 6,764,503 B1 | 7/2004 | Ishimaru |
| 6,764,509 B2 | 7/2004 | Chinn et al. |
| 6,767,345 B2 | 7/2004 | St. Germain et al. |
| 6,773,454 B2 | 8/2004 | Wholey et al. |
| 6,776,791 B1 | 8/2004 | Stallings et al. |
| 6,790,229 B1 | 9/2004 | Berreklouw |
| 6,790,230 B2 | 9/2004 | Beyersdorf et al. |
| 6,790,237 B2 | 9/2004 | Stinson |
| 6,792,979 B2 | 9/2004 | Konya et al. |
| 6,805,675 B1 | 10/2004 | Gardeski et al. |
| 6,814,746 B2 | 11/2004 | Thompson et al. |
| 6,821,282 B2 | 11/2004 | Perry et al. |
| 6,821,297 B2 | 11/2004 | Snyders |
| 6,837,901 B2 | 1/2005 | Rabkin et al. |
| 6,840,957 B2 | 1/2005 | DiMatteo et al. |
| 6,843,802 B1 | 1/2005 | Villalobos et al. |
| 6,849,085 B2 | 2/2005 | Marton |
| 6,855,160 B1 | 2/2005 | Gambale et al. |
| 6,863,668 B2 | 3/2005 | Gillespie et al. |
| 6,872,226 B2 | 3/2005 | Cali et al. |
| 6,875,231 B2 | 4/2005 | Anduiza et al. |
| 6,881,220 B2 | 4/2005 | Edwin et al. |
| 6,887,266 B2 | 5/2005 | Williams et al. |
| 6,890,340 B2 | 5/2005 | Duane |
| 6,893,459 B1 | 5/2005 | Macoviak |
| 6,893,460 B2 | 5/2005 | Spenser et al. |
| 6,905,743 B1 | 6/2005 | Chen et al. |
| 6,908,481 B2 | 6/2005 | Cribier |
| 6,911,036 B2 | 6/2005 | Douk et al. |
| 6,911,043 B2 | 6/2005 | Myers et al. |
| 6,936,058 B2 | 8/2005 | Forde et al. |
| 6,936,067 B2 | 8/2005 | Buchanan |
| 6,953,332 B1 | 10/2005 | Kurk et al. |
| 6,964,673 B2 | 11/2005 | Tsugita et al. |
| 6,974,464 B2 | 12/2005 | Quijano et al. |
| 6,974,474 B2 | 12/2005 | Pavcnik et al. |
| 6,974,476 B2 | 12/2005 | McGuckin, Jr. et al. |
| 6,979,350 B2 | 12/2005 | Moll et al. |
| 6,984,242 B2 | 1/2006 | Campbell et al. |
| 7,011,681 B2 | 3/2006 | Vesely |
| 7,018,406 B2 | 3/2006 | Seguin et al. |
| 7,025,791 B2 | 4/2006 | Levine et al. |
| 7,037,331 B2 | 5/2006 | Mitelberg et al. |
| 7,122,020 B2 | 10/2006 | Mogul |
| 7,166,097 B2 | 1/2007 | Barbut |
| 7,175,653 B2 | 2/2007 | Gaber |
| 7,175,654 B2 | 2/2007 | Bonsignore et al. |
| 7,189,258 B2 | 3/2007 | Johnson et al. |
| 7,191,018 B2 | 3/2007 | Gielen et al. |
| 7,201,772 B2 | 4/2007 | Schwammenthal et al. |
| 7,235,093 B2 | 6/2007 | Gregorich |
| 7,258,696 B2 | 8/2007 | Rabkin et al. |
| 7,318,278 B2 | 1/2008 | Zhang et al. |
| 7,329,279 B2 | 2/2008 | Haug et al. |
| 7,374,560 B2 | 5/2008 | Ressemann et al. |
| 7,381,219 B2 | 6/2008 | Salahieh et al. |
| 7,445,631 B2 | 11/2008 | Salahieh et al. |
| 7,632,298 B2 | 12/2009 | Hijlkema et al. |
| 7,722,666 B2 | 5/2010 | Lafontaine |
| 8,011,067 B2 | 9/2011 | Thompson |
| 8,157,146 B2 | 4/2012 | Edoga et al. |
| 8,172,863 B2 | 5/2012 | Robinson et al. |
| 8,241,344 B2 | 8/2012 | Kusleika et al. |
| 8,663,303 B2 | 3/2014 | Horvath |
| 8,721,702 B2 | 5/2014 | Romoda et al. |
| 8,808,350 B2 | 8/2014 | Schreck |
| 8,951,243 B2 | 2/2015 | Crisostomo et al. |
| 9,131,926 B2 | 9/2015 | Crisostomo et al. |
| 2001/0039450 A1 | 11/2001 | Pavcnik et al. |
| 2001/0041928 A1 | 11/2001 | Pavcnik et al. |
| 2001/0041930 A1 | 11/2001 | Globerman et al. |
| 2001/0044634 A1 | 11/2001 | Don Michael et al. |
| 2001/0044652 A1 | 11/2001 | Moore |
| 2001/0044656 A1 | 11/2001 | Williamson, IV et al. |
| 2002/0002396 A1 | 1/2002 | Fulkerson |

(56) References Cited

U.S. PATENT DOCUMENTS

| | | |
|---|---|---|
| 2002/0010489 A1 | 1/2002 | Grayzel et al. |
| 2002/0026233 A1 | 2/2002 | Shaknovich |
| 2002/0029981 A1 | 3/2002 | Nigam |
| 2002/0032481 A1 | 3/2002 | Gabbay |
| 2002/0055769 A1 | 5/2002 | Wang |
| 2002/0058995 A1 | 5/2002 | Stevens |
| 2002/0077696 A1 | 6/2002 | Zadno-Azizi et al. |
| 2002/0082609 A1 | 6/2002 | Green |
| 2002/0095173 A1 | 7/2002 | Mazzocchi et al. |
| 2002/0095209 A1 | 7/2002 | Zadno-Azizi et al. |
| 2002/0111674 A1 | 8/2002 | Chouinard et al. |
| 2002/0120328 A1 | 8/2002 | Pathak et al. |
| 2002/0151970 A1 | 10/2002 | Garrison et al. |
| 2002/0161392 A1 | 10/2002 | Dubrul |
| 2002/0161394 A1 | 10/2002 | Macoviak et al. |
| 2002/0177766 A1 | 11/2002 | Mogul |
| 2002/0188341 A1 | 12/2002 | Elliott |
| 2002/0188344 A1 | 12/2002 | Bolea et al. |
| 2003/0023303 A1 | 1/2003 | Palmaz et al. |
| 2003/0036791 A1 | 2/2003 | Philipp et al. |
| 2003/0040771 A1 | 2/2003 | Klyodoh et al. |
| 2003/0040772 A1 | 2/2003 | Klyodoh et al. |
| 2003/0040791 A1 | 2/2003 | Oktay |
| 2003/0050694 A1 | 3/2003 | Yang et al. |
| 2003/0055495 A1 | 3/2003 | Pease et al. |
| 2003/0060844 A1 | 3/2003 | Borillo et al. |
| 2003/0070944 A1 | 4/2003 | Nigam |
| 2003/0109924 A1 | 6/2003 | Cribier |
| 2003/0109930 A1 | 6/2003 | Bluni et al. |
| 2003/0114912 A1 | 6/2003 | Sequin et al. |
| 2003/0125795 A1 | 7/2003 | Pavcnik et al. |
| 2003/0130729 A1 | 7/2003 | Paniagua et al. |
| 2003/0135257 A1 | 7/2003 | Taheri |
| 2003/0144732 A1 | 7/2003 | Cosgrove et al. |
| 2003/0149476 A1 | 8/2003 | Damm et al. |
| 2003/0149478 A1 | 8/2003 | Figulla et al. |
| 2003/0176884 A1 | 9/2003 | Berrada et al. |
| 2003/0181850 A1 | 9/2003 | Diamond et al. |
| 2003/0187495 A1 | 10/2003 | Cully et al. |
| 2003/0199913 A1 | 10/2003 | Dubrul et al. |
| 2003/0199971 A1 | 10/2003 | Tower et al. |
| 2003/0199972 A1 | 10/2003 | Zadno-Azizi et al. |
| 2003/0208224 A1 | 11/2003 | Broome |
| 2003/0212429 A1 | 11/2003 | Keegan et al. |
| 2003/0212452 A1 | 11/2003 | Zadno-Azizi et al. |
| 2003/0212454 A1 | 11/2003 | Scott et al. |
| 2003/0216774 A1 | 11/2003 | Larson |
| 2003/0225445 A1 | 12/2003 | Derus et al. |
| 2003/0229390 A1 | 12/2003 | Ashton et al. |
| 2003/0233117 A1 | 12/2003 | Adams et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049226 A1 | 3/2004 | Keegan et al. |
| 2004/0049262 A1 | 3/2004 | Obermiller et al. |
| 2004/0073198 A1 | 4/2004 | Gilson et al. |
| 2004/0082904 A1 | 4/2004 | Houde et al. |
| 2004/0082967 A1 | 4/2004 | Broome et al. |
| 2004/0087982 A1 | 5/2004 | Eskuri |
| 2004/0088045 A1 | 5/2004 | Cox |
| 2004/0093016 A1 | 5/2004 | Root et al. |
| 2004/0098022 A1 | 5/2004 | Barone |
| 2004/0098099 A1 | 5/2004 | McCullagh et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0127979 A1 | 7/2004 | Wilson et al. |
| 2004/0133274 A1 | 7/2004 | Webler et al. |
| 2004/0138694 A1 | 7/2004 | Tran et al. |
| 2004/0138742 A1 | 7/2004 | Myers et al. |
| 2004/0148021 A1 | 7/2004 | Cartledge et al. |
| 2004/0153094 A1 | 8/2004 | Dunfee et al. |
| 2004/0158277 A1 | 8/2004 | Lowe et al. |
| 2004/0167565 A1 | 8/2004 | Beulke et al. |
| 2004/0181140 A1 | 9/2004 | Falwell et al. |
| 2004/0186563 A1 | 9/2004 | Lobbi |
| 2004/0204755 A1 | 10/2004 | Robin |
| 2004/0215331 A1 | 10/2004 | Chew et al. |
| 2004/0215339 A1 | 10/2004 | Drasler et al. |
| 2004/0220655 A1 | 11/2004 | Swanson et al. |
| 2004/0225321 A1 | 11/2004 | Krolik et al. |
| 2004/0254636 A1 | 12/2004 | Flagle et al. |
| 2005/0033402 A1 | 2/2005 | Cully et al. |
| 2005/0043711 A1 | 2/2005 | Corcoran et al. |
| 2005/0075662 A1 | 4/2005 | Pedersen et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0090834 A1 | 4/2005 | Chiang et al. |
| 2005/0090846 A1 | 4/2005 | Pedersen et al. |
| 2005/0096692 A1 | 5/2005 | Linder et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0100580 A1 | 5/2005 | Osborne et al. |
| 2005/0107822 A1 | 5/2005 | WasDyke |
| 2005/0113910 A1 | 5/2005 | Paniagua et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137691 A1 | 6/2005 | Salahieh et al. |
| 2005/0137692 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0143809 A1 | 6/2005 | Salahieh et al. |
| 2005/0165352 A1 | 7/2005 | Henry et al. |
| 2005/0165477 A1 | 7/2005 | Anduiza et al. |
| 2005/0182486 A1 | 8/2005 | Gabbay |
| 2005/0197694 A1 | 9/2005 | Pai et al. |
| 2005/0197695 A1 | 9/2005 | Stacchino et al. |
| 2005/0203614 A1 | 9/2005 | Forster et al. |
| 2005/0203615 A1 | 9/2005 | Forster et al. |
| 2005/0203616 A1 | 9/2005 | Cribier |
| 2005/0203617 A1 | 9/2005 | Forster et al. |
| 2005/0209580 A1 | 9/2005 | Freyman |
| 2005/0228472 A1 | 10/2005 | Case et al. |
| 2005/0251250 A1 | 11/2005 | Verhoeven et al. |
| 2005/0251251 A1 | 11/2005 | Cribier |
| 2005/0261759 A1 | 11/2005 | Lambrecht et al. |
| 2005/0267560 A1 | 12/2005 | Bates |
| 2005/0283231 A1 | 12/2005 | Haug et al. |
| 2005/0283962 A1 | 12/2005 | Boudjemline |
| 2006/0004439 A1 | 1/2006 | Spenser et al. |
| 2006/0004442 A1 | 1/2006 | Spenser et al. |
| 2006/0015168 A1 | 1/2006 | Gunderson |
| 2006/0058872 A1 | 3/2006 | Salahieh et al. |
| 2006/0155312 A1 | 7/2006 | Levine et al. |
| 2006/0161249 A1 | 7/2006 | Realyvasquez et al. |
| 2006/0173524 A1 | 8/2006 | Salahieh et al. |
| 2006/0195183 A1 | 8/2006 | Navia et al. |
| 2006/0253191 A1 | 11/2006 | Salahieh et al. |
| 2006/0259134 A1 | 11/2006 | Schwammenthal et al. |
| 2006/0271166 A1 | 11/2006 | Thill et al. |
| 2006/0287668 A1 | 12/2006 | Fawzi et al. |
| 2007/0010876 A1 | 1/2007 | Salahieh et al. |
| 2007/0010877 A1 | 1/2007 | Salahieh et al. |
| 2007/0016286 A1 | 1/2007 | Herrmann et al. |
| 2007/0055340 A1 | 3/2007 | Pryor |
| 2007/0061008 A1 | 3/2007 | Salahieh et al. |
| 2007/0112355 A1 | 5/2007 | Salahieh et al. |
| 2007/0118214 A1 | 5/2007 | Salahieh et al. |
| 2007/0162107 A1 | 7/2007 | Haug et al. |
| 2007/0203503 A1 | 8/2007 | Salahieh et al. |
| 2007/0244552 A1 | 10/2007 | Salahieh et al. |
| 2007/0244555 A1 | 10/2007 | Ratiee et al. |

(56) References Cited

U.S. PATENT DOCUMENTS

| | | |
|---|---|---|
| 2007/0288089 A1 | 12/2007 | Gurskis et al. |
| 2008/0082165 A1 | 4/2008 | Wilson et al. |
| 2008/0109059 A1 | 5/2008 | Gordon et al. |
| 2008/0114435 A1 | 5/2008 | Bowe |
| 2008/0125859 A1 | 5/2008 | Salahieh et al. |
| 2008/0154244 A1 | 6/2008 | Singh |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0234814 A1 | 9/2008 | Salahieh et al. |
| 2008/0255542 A1 | 10/2008 | Nimgaard et al. |
| 2008/0255588 A1 | 10/2008 | Hinman |
| 2008/0288054 A1 | 11/2008 | Pulnev et al. |
| 2009/0005863 A1 | 1/2009 | Goetz et al. |
| 2009/0018507 A1 | 1/2009 | Schmitz et al. |
| 2009/0054969 A1 | 2/2009 | Salahieh et al. |
| 2009/0076598 A1 | 3/2009 | Salahieh et al. |
| 2009/0171456 A1 | 7/2009 | Kveen et al. |
| 2009/0222076 A1 | 9/2009 | Figulla et al. |
| 2009/0254165 A1 | 10/2009 | Tabor et al. |
| 2009/0264759 A1 | 10/2009 | Byrd |
| 2009/0264997 A1 | 10/2009 | Haug et al. |
| 2009/0326566 A1 | 12/2009 | Alvarado |
| 2010/0010293 A1 | 1/2010 | Sato |
| 2010/0030237 A1 | 2/2010 | Hayashi et al. |
| 2010/0030255 A1 | 2/2010 | Berra et al. |
| 2010/0049313 A1 | 2/2010 | Alon et al. |
| 2010/0121434 A1 | 5/2010 | Paul et al. |
| 2010/0191326 A1 | 7/2010 | Alkhatib |
| 2010/0217274 A1 | 8/2010 | Lee et al. |
| 2010/0219092 A1 | 9/2010 | Salahieh et al. |
| 2010/0249915 A1 | 9/2010 | Zhang |
| 2010/0249916 A1 | 9/2010 | Zhang |
| 2010/0249917 A1 | 9/2010 | Zhang |
| 2010/0249918 A1 | 9/2010 | Zhang |
| 2010/0256725 A1 | 10/2010 | Ramussen |
| 2010/0256727 A1 | 10/2010 | Gerdts et al. |
| 2010/0274340 A1 | 10/2010 | Hartley et al. |
| 2011/0054585 A1 | 3/2011 | Osborne |
| 2011/0088519 A1 | 4/2011 | Hu |
| 2011/0208296 A1 | 8/2011 | Duffy |
| 2011/0257718 A1 | 10/2011 | Argentine |
| 2011/0264074 A1 | 10/2011 | Tegg et al. |
| 2011/0270372 A1 | 11/2011 | Argentine |
| 2011/0282425 A1 | 11/2011 | Dwork |
| 2011/0295216 A1 | 12/2011 | Miller |
| 2011/0307049 A1 | 12/2011 | Kao |
| 2012/0016468 A1 | 1/2012 | Robin et al. |
| 2012/0035717 A1 | 2/2012 | Duffy et al. |
| 2012/0041547 A1 | 2/2012 | Duffy et al. |
| 2012/0078076 A1 | 3/2012 | Stewart et al. |
| 2012/0103840 A1 | 5/2012 | McCaffrey |
| 2012/0136425 A1 | 5/2012 | Orr |
| 2012/0172968 A1 | 7/2012 | Chuter et al. |
| 2012/0239142 A1 | 9/2012 | Liu et al. |
| 2012/0245606 A1 | 9/2012 | Goldberg et al. |
| 2012/0271398 A1 | 10/2012 | Essinger et al. |
| 2012/0290066 A1 | 11/2012 | Nabulsi et al. |
| 2012/0296407 A1 | 11/2012 | Caselnova |
| 2012/0305441 A1 | 12/2012 | Murray et al. |
| 2012/0310332 A1 | 12/2012 | Murray et al. |
| 2013/0123757 A1 | 5/2013 | Crisostomo et al. |
| 2013/0123796 A1 | 5/2013 | Sutton et al. |
| 2013/0123898 A1 | 5/2013 | Tung et al. |
| 2013/0123912 A1 | 5/2013 | Tung et al. |
| 2013/0131774 A1 | 5/2013 | Nabulsi et al. |
| 2013/0144276 A1 | 6/2013 | Crisostomo et al. |
| 2013/0158653 A1 | 6/2013 | Gamarra et al. |
| 2013/0158655 A1 | 6/2013 | Sutton et al. |

FOREIGN PATENT DOCUMENTS

| | | | |
|---|---|---|---|
| EP | 0409929 B1 | 4/1997 | |
| EP | 1000590 A1 | 5/2000 | |
| EP | 1057459 A1 | 12/2000 | |
| EP | 1057460 A1 | 12/2000 | |
| EP | 0937439 B1 | 9/2003 | |
| EP | 1340473 A2 | 9/2003 | |
| EP | 1356793 A2 | 10/2003 | |
| EP | 1042045 B1 | 5/2004 | |
| EP | 0819013 B1 | 6/2004 | |
| EP | 1430853 A2 | 6/2004 | |
| EP | 1229864 B1 | 4/2005 | |
| EP | 1059894 B1 | 7/2005 | |
| EP | 1078610 B1 | 8/2005 | |
| EP | 1576937 A2 | 9/2005 | |
| EP | 1582178 A2 | 10/2005 | |
| EP | 1582179 A2 | 10/2005 | |
| EP | 1600121 A1 | 11/2005 | |
| EP | 1156757 B1 | 12/2005 | |
| EP | 1616531 A2 | 1/2006 | |
| WO | 9315693 A1 | 8/1993 | |
| WO | 9504556 A2 | 2/1995 | |
| WO | 9529640 A1 | 11/1995 | |
| WO | 9614032 A1 | 5/1996 | |
| WO | 9624306 A1 | 8/1996 | |
| WO | 9836790 A1 | 8/1998 | |
| WO | 9850103 A1 | 11/1998 | |
| WO | 9857599 A2 | 12/1998 | |
| WO | 9905975 A1 | 2/1999 | |
| WO | 9944542 A2 | 9/1999 | |
| WO | 0009059 A2 | 2/2000 | |
| WO | 0044308 A2 | 8/2000 | |
| WO | 0044313 A1 | 8/2000 | |
| WO | 0049970 A1 | 8/2000 | |
| WO | 0067661 A1 | 11/2000 | |
| WO | 0105331 A1 | 1/2001 | |
| WO | 0108596 A1 | 2/2001 | |
| WO | 0110320 A1 | 2/2001 | |
| WO | 0110343 A1 | 2/2001 | |
| WO | 0135870 A1 | 5/2001 | |
| WO | 0164137 A1 | 9/2001 | |
| WO | 0236048 A1 | 5/2002 | |
| WO | 0239910 A2 | 5/2002 | |
| WO | 0241789 A2 | 5/2002 | |
| WO | 02100297 A2 | 12/2002 | |
| WO | 03003943 A2 | 1/2003 | |
| WO | 03003949 A2 | 1/2003 | |
| WO | 03011195 A2 | 2/2003 | |
| WO | 03030776 A2 | 4/2003 | |
| WO | 03015851 B1 | 11/2003 | |
| WO | 03094797 A1 | 11/2003 | |
| WO | 2004014256 A1 | 2/2004 | |
| WO | 2004019811 A2 | 3/2004 | |
| WO | 2004019825 A1 | 3/2004 | |
| WO | 2004023980 A2 | 3/2004 | |
| WO | 2004026117 A2 | 4/2004 | |
| WO | 2004041126 A1 | 5/2004 | |
| WO | 2004047681 A1 | 6/2004 | |
| WO | 2004066876 A1 | 8/2004 | |
| WO | 2004082536 A1 | 9/2004 | |
| WO | 2005084595 A1 | 9/2005 | |
| WO | 2005087140 A1 | 9/2005 | |
| WO | 2012155130 A1 | 11/2012 | |
| WO | WO2015/014932 | * 2/2015 | ............... A61B 2/24 |

OTHER PUBLICATIONS

Invitation to Pay Additional Fees and, Where Applicable, Protest Fee, PCT/US2016/049693, dated Nov. 9, 2016.

Andersen et al., "Transluminal implantation of artificial heart valves. Description of a new expandable aortic valve and initial results with implantation by catheter technique in closed chest pigs," Euro. Heart J., vol. 13:704-708, May 1992.

Atwood et al., "Insertion of Heart Valves by Catheterization," Project Supervised by Prof. S. Muftu of Northeastern University 2001-2002, pp. 36-40, May 30, 2002.

Bodnar et al., "Replacement Cardiac Valves R Chapter 13: Extinct cardiac valve prostheses," Pergamon Publishing Corporation, New York, pp. 307-322, 1991.

(56) References Cited

OTHER PUBLICATIONS

Boudjemline et al., "Percutaneous implantation of a biological valve in the aorta to treat aortic valve insufficiency—a sheep study," Med Sci. Monit.,vol. 8(4): BR113-116, Apr. 12, 2002.
Boudjemline et al., "Percutaneous implantation of a valve in the descending aorta in lambs," Euro. Heart J., vol. 23: 1045-1049, Jul. 2002.
Boudjemline et al., "Percutaneous pulmonary valve replacement in a large right ventricular outflow tract: an experimental study," Journal of the American College of Cardiology, vol. 43(6): 1082-1087, Mar. 17, 2004.
Boudjemline et al., "Percutaneous valve insertion: A new approach?," J. of Thoracic and Cardio. Sugr., vol. 125(3): 741-743, Mar. 2003.
Boudjemline et al., "Steps Toward Percutaneous Aortic Valve Replacement," Circulation, vol. 105:775-778, Feb. 12, 2002.
Cribier et al., "Early Experience with Percutaneous Transcatheter Implantation of Heart Valve Prosthesis for the Treatment of End-Stage Inoperable Patents with Calcific Aortic Stenosis," J. of Am. Coll. Of Cardio., vol. 43(4): 698-703, Feb. 18, 2004.
Cribier et al., "Percutaneous Transcatheter Implantation of an Aortic Valve Prosthesis for Calcific Aortic Stenosis: First Human Case Description," Circulation, vol. 106: 3006-3008, Dec. 10, 2002.
Cribier et al., "Percutaneous Transcatheter Implantation of an Aortic Valve Prosthesis for Calcitic Aortic Stenosis: First Human Case," Percutaneous Valve Technologies, Inc.,16 pages, Apr. 16, 2002.
Ferrari et al., "Percutaneous transvascular aortic valve replacement with self expanding stent-valve device," Poster from the presentation given at SMIT 2000, 12th International Conference, Sep. 5, 2000.
Hijazi, "Transcatheter Valve Replacement: A New Era of Percutaneous Cardiac Intervention Begins," J. of Am. College of Cardio. 2-4, vol. 43(6): 1088-1089, Mar. 17, 2004.
Huber et al., "Do valved stents compromise coronary flow?," European Journal of Cardio-thoracic Surgery. 2-4, vol. 25: 754-759, Jan. 23, 2004.
Knudsen et al., "Catheter-implanted prosthetic heart valves," Int'l J. of Art. Organs, vol. 16(5): 253-262, May 1993.
Kort et al., "Minimally invasive aortic valve replacement: Echocardiographic and clinical results," Am Heart J., vol. 142(3): 476-481, Sep. 2001.
Love et al., "The Autogenous Tissue Heart Valve: Current Stat," Journal of Cardiac Surgery, vol. 6(4): 499-507, Mar. 1991.
Lutter et al., "Percutaneous aortic valve replacement: An experimental study. I. Studies on implantation," J. of Thoracic and Cardio. Surg., vol. 123(4): 768-776, Apr. 2002.
Moulopoulos et al. "Catheter-Mounted Aortic Valves," Annals of Thoracic Surg., vol. 11(5): 423-430, May 1971.
Paniagua et al., "Percutaneous heart valve in the chronic in vitro testing model," Circulation., vol. 106: e51-e52, Sep. 17, 2002.
Paniagua et al., "Heart Watch (2004)," Texas Heart Institute, 8 pages, Spring, 2004 Edition.
Pavcnik et al., "Percutaneous bioprosthetic veno valve: A long-term study in sheep," J. of Vascular Surg., vol. 35(3): 598-603, Mar. 2002.
Phillips et al., "A Temporary Catheter-Tip Aortic Valve: Hemodynamic Effects on Experimental Acute Aortic Insufficiency," Annals of Thoracic Surg., vol. 21(2): 134-136, Feb. 1976.
Sochman et al., "Percutaneous Transcatheter Aortic Disc Valve Prosthesis Implantation: A Feasibility Study," Cardiovasc. Intervent. Radiol., vol. 23: 384-388, Sep. 2000.
Stuart, "In Heart Valves, A Brave, New Non-Surgical World," Start-Up, pp. 9-17, Feb. 2004.
Vahanian et al, "Percutaneous Approaches to Valvular Disease," Circulation, vol. 109: 1572-1579, Apr. 6, 2004.
Van Herwerden et al., "Percutaneous valve implantation: back to the future?," Euro. Heart J., vol. 23(18): 1415-1416, Sep. 2002.
Zhou et al., "Self-expandable valved stent of large size: off-bypass implantation in pulmonary position," Eur. J. Cardiothorac, vol. 24: 212-216, Aug. 2003.
Paul et al., U.S. Appl. No. 12/578,463 entitled "Medical Devices and Delivery Systems for Delivering Medical Devices," filed Oct. 13, 2009.

\* cited by examiner

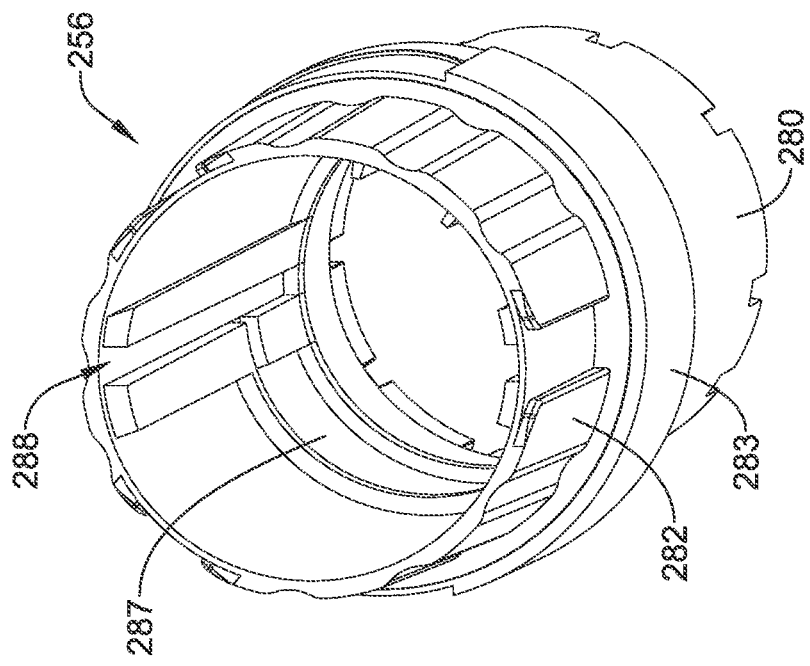
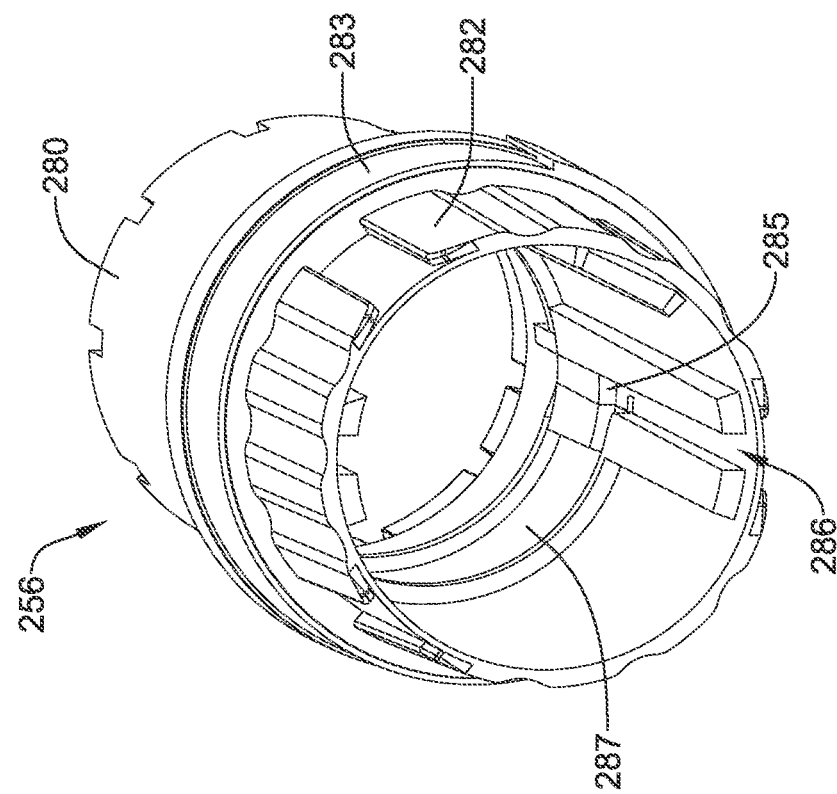
Figure 14

MEDICAL DEVICE HANDLE

CROSS-REFERENCE TO RELATED APPLICATIONS

The present application claims the benefit of and priority to U.S. Provisional Patent Application Ser. No. 62/213,931, filed Sep. 3, 2015, the disclosure of which is incorporated herein by reference.

BACKGROUND

Medical devices typically used for cardiovascular system treatments may involve complex and invasive therapies resulting is significant discomfort, pain, and long recovery times for patients. Recently, less invasive, percutaneous treatments have been developed. There is an ongoing need for improved, less invasive cardiovascular treatments.

SUMMARY

In a first aspect, a medical device handle for percutaneous delivery of a medical device implant may comprise an elongated handle housing having a proximal end, a distal end, and a longitudinal axis extending from the proximal end to the distal end; a rotatable collar disposed about the proximal end of the elongated handle housing; and a rotatable control knob disposed about a proximal portion of the rotatable collar. The rotatable collar may include a first internally-facing longitudinal slot extending less than a full length of the rotatable collar and terminating proximally at a distally-facing wall of an internally-facing circumferentially-oriented slot. The rotatable control knob may be configured to actuate the medical device implant between a delivery configuration, a deployed configuration, and a released configuration.

In addition or alternatively, and in a second aspect, the medical device implant is reversibly actuatable between the delivery configuration and the deployed configuration.

In addition or alternatively, and in a third aspect, the internally-facing circumferentially-oriented slot operatively connects the first internally-facing longitudinal slot with a second internally-facing longitudinal slot extending both proximally and distally from the internally-facing circumferentially-oriented slot.

In addition or alternatively, and in a fourth aspect, the elongated handle housing includes an axial translation mechanism disposed therein and operatively connected to the rotatable control knob.

In addition or alternatively, and in a fifth aspect, the axial translation mechanism converts rotational motion of the rotatable control knob into axial translation of a carriage element disposed within the elongated handle housing.

In addition or alternatively, and in a sixth aspect, the carriage element includes a laterally-extending protrusion configured to engage with the rotatable collar.

In addition or alternatively, and in a seventh aspect, the rotatable collar is prevented from rotating when the laterally-extending protrusion is engaged with the first internally-facing longitudinal slot.

In addition or alternatively, and in an eighth aspect, the laterally-extending protrusion is engaged with a distal portion of the first internally-facing longitudinal slot when the medical device implant is in the delivery configuration.

In addition or alternatively, and in a ninth aspect, the laterally-extending protrusion is engaged with the internally-facing circumferentially-oriented slot when the medical device implant is in the deployed configuration.

In addition or alternatively, and in a tenth aspect, the laterally-extending protrusion is engaged with a proximal portion of the second internally-facing longitudinal slot when the medical device implant is in the released configuration.

In addition or alternatively, and in an eleventh aspect, the medical device handle may further include a release ring engaged with the rotatable collar that is axially translatable from a first position to a second position, the release ring including an arm extending within the rotatable collar and engaged with the first internally-facing longitudinal slot.

In addition or alternatively, and in a twelfth aspect, the arm prevents the laterally-extending protrusion from accessing the internally-facing circumferentially-oriented slot from the first internally-facing longitudinal slot when the release ring is in the first position.

In addition or alternatively, and in a thirteenth aspect, a plurality of compression springs biases the release ring distally relative to the rotatable collar.

In addition or alternatively, and in a fourteenth aspect, proximal translation of the release ring relative to the rotatable collar shifts the release ring from the first position to the second position, thereby permitting the laterally-extending protrusion to access the internally-facing circumferentially-oriented slot from the first internally-facing longitudinal slot.

In addition or alternatively, and in a fifteenth aspect, the elongated handle housing includes a locking clip configured to engage an opening in the carriage element when the carriage element is axially translated to its proximalmost position, the locking clip preventing distal translation of at least a portion of the carriage element after engaging the opening in the carriage element.

In addition or alternatively, and in a sixteenth aspect, a medical device handle for percutaneous delivery of a medical device implant may comprise an elongated handle housing having a proximal end, a distal end, and a longitudinal axis extending from the proximal end to the distal end; a rotatable control knob disposed about the proximal end of the elongated handle housing; and a carriage element disposed within the elongated handle housing having a plurality of tracks formed in an exterior surface thereof. The carriage element may be movable relative to the elongated handle housing through rotation of the rotatable control knob. The rotatable control knob may be configured to actuate the medical device implant between a delivery configuration, a deployed configuration, and a released configuration.

In addition or alternatively, and in a seventeenth aspect, the plurality of tracks includes a first track and a second track, the first track being distinct from the second track.

In addition or alternatively, and in an eighteenth aspect, the first track is configured to engage a cam block extending from the elongated handle housing, and the second track is configured to engage an actuator member extending to the medical device implant.

In addition or alternatively, and in a nineteenth aspect, translation of the cam block at least partially along the first track actuates the medical device implant from the delivery configuration to the deployed configuration.

In addition or alternatively, and in a twentieth aspect, translation of the actuator member along the second track actuates the medical device implant from the deployed configuration to the released configuration.

BRIEF DESCRIPTION OF THE DRAWINGS

The invention may be more completely understood in consideration of the following detailed description of various embodiments of the invention in connection with the accompanying drawings, in which:

FIG. 14 illustrates an example collar of the example medical device handle of FIG. 4;

Figure 1:
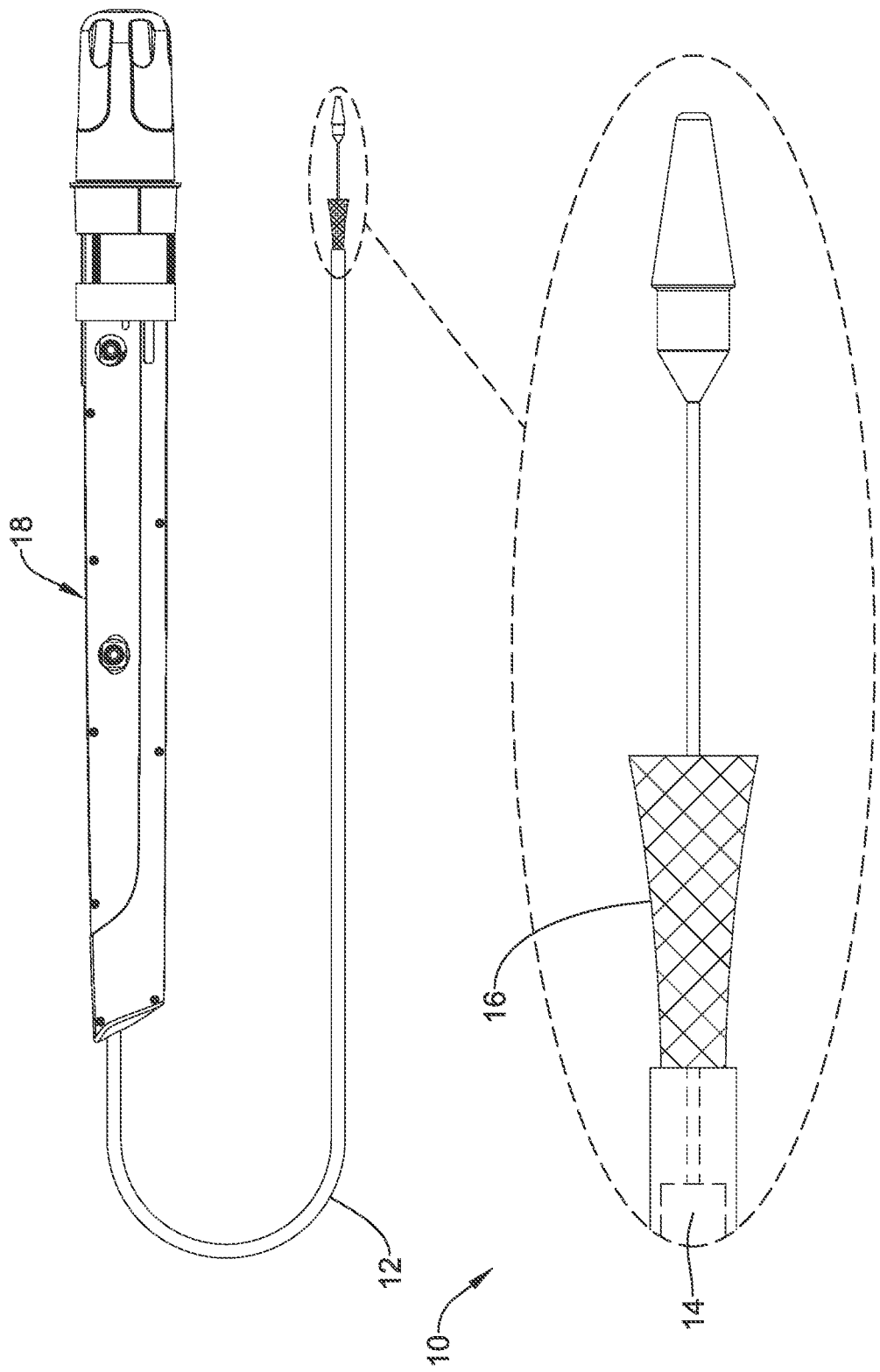
FIG. 1 schematically illustrates an example medical device system.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g. 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Relative terms such as "proximal", "distal", "advance", "retract", variants thereof, and the like, may be generally be considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Diseases and/or medical conditions that impact the cardiovascular system are prevalent in the United States and throughout the world. Traditionally, treatment of the cardiovascular system was often conducted by directly accessing the impacted part of the system. For example, treatment of a blockage in one or more of the coronary arteries was traditionally treated using coronary artery bypass surgery. As can be readily appreciated, such therapies are rather invasive to the patient and require significant recovery times and/or treatments. More recently, less invasive therapies have been developed, for example, where a blocked coronary artery could be accessed and treated via a percutaneous catheter (e.g., angioplasty). Such therapies have gained wide acceptance among patients and clinicians.

Some relatively common medical conditions may include or be the result of inefficiency, ineffectiveness, or complete failure of one or more of the valves within the heart. For example, failure of the aortic valve can have a serious effect on a human and could lead to serious health condition and/or death if not dealt with. Treatment of defective heart valves poses other challenges in that the treatment often requires the repair or outright replacement of the defective valve. Such therapies may be highly invasive to the patient. Disclosed herein are medical devices that may be used for delivering a medical device to a portion of the cardiovascular system in order to diagnose, treat, and/or repair the system. At least some of the medical devices disclosed herein may be used to deliver and implant a replacement heart valve (e.g., a replacement aortic valve). In addition, the devices disclosed herein may deliver the replacement heart valve percutaneously and, thus, may be much less invasive to the patient. The devices disclosed herein may also provide a number of additional desirable features and benefits as described in more detail below.

FIG. 1 schematically illustrates an example medical device system 10. It should be noted that some features of the medical device system 10 are either not shown, or are shown schematically, in FIG. 1 for simplicity. Additional details regarding some of the components of the medical device system 10 are provided in other figures in greater detail. A medical device system 10 may be used to deliver and/or deploy a variety of medical devices to a number of locations within the anatomy. In at least some embodiments, the medical device system 10 may be a replacement heart valve system (e.g., a replacement aortic valve system) that can be used for percutaneous delivery of a replacement heart valve. This, however, is not intended to be limiting as the medical device system 10 may also be used for other interventions including mitral valve replacement, valve repair, valvuloplasty, and the like, or other similar interventions.

The medical device system 10 may generally be described as a catheter system that includes an outer sheath 12, an inner catheter 14 (a portion of which is shown in FIG. 1 in phantom line) extending at least partially through a lumen of the outer sheath 12, and a medical device implant 16 (e.g., a replacement heart valve, for example, which term may be used interchangeably with the term "medical device implant" herein) which may be coupled to the inner catheter 14 and disposed within a lumen of the outer sheath 12 during delivery of the medical device implant 16. In some embodiments, a medical device handle 18 may be disposed at a proximal end of the outer sheath 12 and/or the inner catheter 14 and may include one or more actuation means associated therewith. In general, the medical device handle 18 may be configured to manipulate the position of the outer sheath 12 relative to the inner catheter 14 and/or aid in the deployment of the medical device implant 16.

Figure 2:
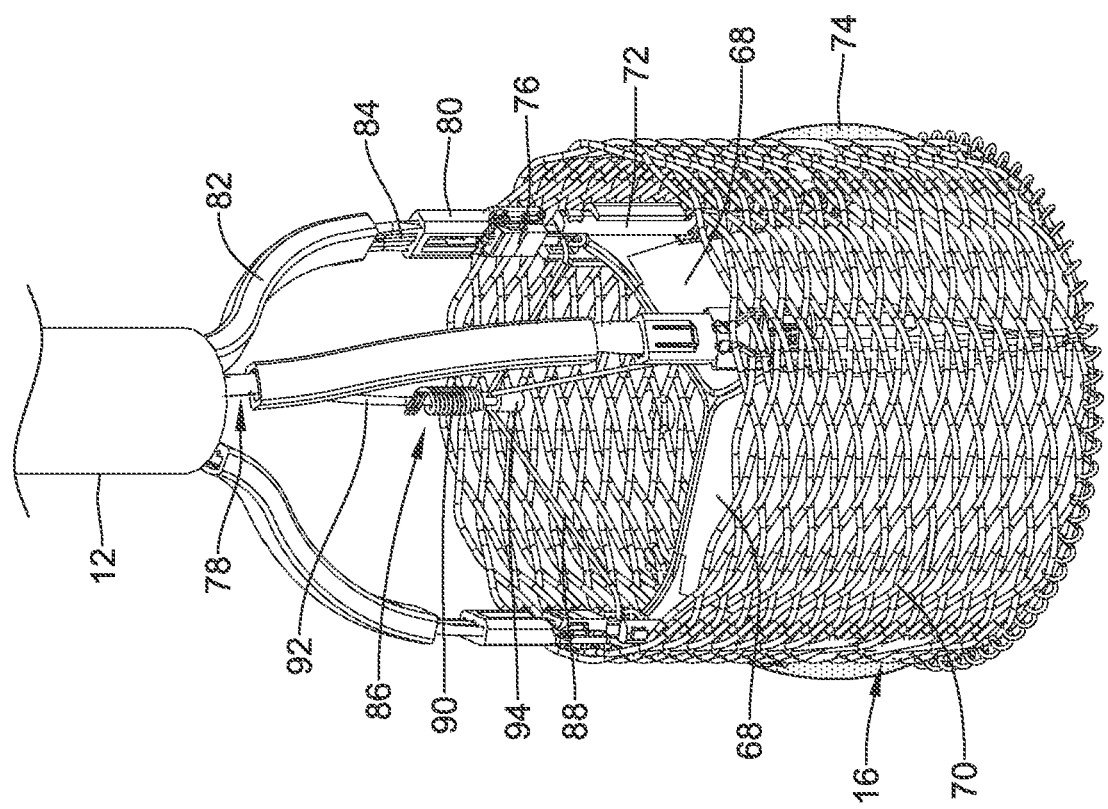
FIG. 2 is a perspective view of a portion of an example medical device implant associated with the example medical device system.
Figure 3:
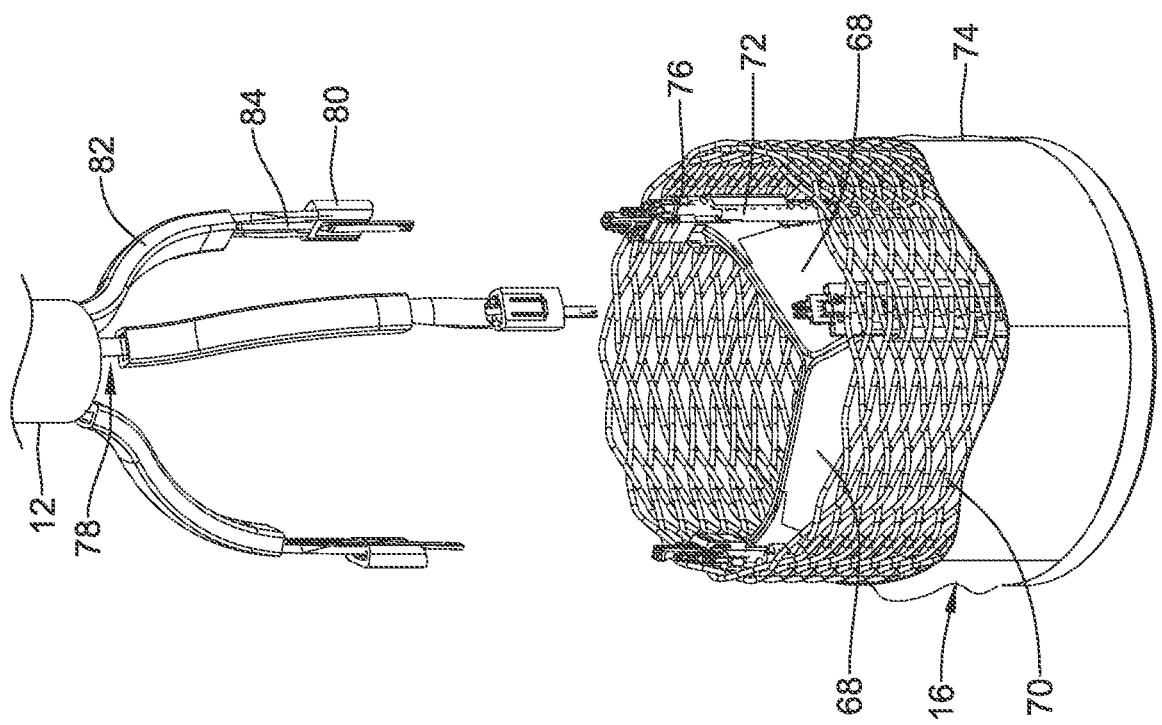
FIG. 3 is a perspective view of a portion of an example medical device implant associated with the example medical device system.

In use, the medical device system 10 may be advanced percutaneously through the vasculature to a position adjacent to an area of interest and/or a treatment location. For example, in some embodiments, the medical device system 10 may be advanced through the vasculature and across the aortic arch to a position adjacent to a defective aortic valve. In some embodiments, the medical device system 10 may be advanced to a position adjacent another heart valve (e.g., mitral valve, etc.). Alternative approaches to treat a defective aortic valve and/or other heart valve(s) are also contemplated with the medical device system 10. During delivery, the medical device implant 16 may be generally disposed in an elongated and low profile "delivery" configuration within the lumen and/or a distal end of the outer sheath 12, as seen schematically in FIG. 1 for example. Once positioned, the outer sheath 12 may be retracted relative to the medical device implant 16 and/or the inner catheter 14 to expose the medical device implant 16. In some embodiments, the medical device implant 16 may be disposed in an "everted" configuration or a partially-everted configuration while disposed within the lumen and/or the distal end of the outer sheath 12 and/or immediately upon exposure after retracting the outer sheath 12. In some embodiments, the "delivery" configuration and the "everted" configuration may be substantially similar and/or may be used interchangeably. The medical device implant 16 may be actuated using the medical device handle 18 in order to translate the medical device implant 16 into a generally shortened and larger profile "deployed" configuration suitable for implantation within the anatomy, as seen in FIG. 2 for example. When the medical device implant 16 is suitably deployed within the anatomy, the medical device system 10 may be disconnected from the medical device implant 16 and the medical device system 10 can be removed from the vasculature, leaving the medical device implant 16 in place in a "released" configuration, as seen in FIG. 3 for example, to function as, for example, a suitable replacement for the native aortic valve. In at least some interventions, the medical device implant 16 may be deployed within the native valve (e.g., the native valve is left in place and not excised). Alternatively, the native valve may be removed and the medical device implant 16 may be deployed in its place as a replacement.

In some embodiments, the outer sheath 12 may be formed from a singular monolithic tube or unitary member having a lumen extending longitudinally therethrough. Alternatively, the outer sheath 12 may include a plurality of layers or portions. One or more of these layers may include a reinforcing structure such as a braid, coil, mesh, combinations thereof, or the like. Several alternative structural configurations are contemplated for the outer sheath 12 including embodiments including embodiments without a reinforcement, or other suitable configurations. In some embodiments, the reinforcing structure may take the form of a braid, coil, mesh, or the like. For example, in some embodiments, the reinforcing structure may include a metallic braid (e.g., stainless steel). In some of these embodiments, the reinforcing structure may also include additional structures such as one or more longitudinally-extending strands. For example, the reinforcing structure may include a pair of longitudinally-extending aramid and/or para aramid strands (for example, KEVLAR®) disposed on opposite sides of the braid. These strands may or may not be woven into portions or all of the braid.

In some embodiments, the inner catheter 14 may take the form of an extruded polymer tube. Other forms are also contemplated including other polymer tubes, metallic tubes, reinforced tubes, or the like including other suitable materials such as those disclosed herein. In some embodiments, the inner catheter 14 may be a singular monolithic or unitary member. In other embodiments, the inner catheter 14 may include a plurality of portions or segments that are coupled together. In some embodiments, the inner catheter 14 may also be curved, for example adjacent to the distal end thereof. In some embodiments, the inner catheter 14 may have one or more sections with a differing hardness/stiffness (e.g., differing shore durometer). In some embodiments, the inner catheter 14 may include one or more lumens extending longitudinally through the inner catheter 14. For example, the inner catheter 14 may include a first lumen, a second lumen, a third lumen, and a fourth lumen. In general, the lumens may extend along an entire length of the inner catheter 14. Other embodiments are contemplated, however, where one or more of the lumens extend along only a portion of the length of the inner catheter 14. For example, in some embodiments, the fourth lumen may extend distally from a proximal end of the inner catheter and stop just short of the distal end of the inner catheter 14 and/or be filled in at its distal end to effectively end the fourth lumen proximal of the distal end of the inner catheter 14.

In some embodiments, disposed within the first lumen may be at least one actuator member 84, which may be used to actuate (i.e., expand and/or elongate) the medical device implant 16 between a delivery configuration and a deployed configuration, as explained in more detail herein. For the purposes of this disclosure and any related proceedings, the terms "actuator member" and "push-pull rod" (including both singular and plural forms thereof) may be used interchangeably herein. In some embodiments, the medical device system 10 may include at least one actuator member 84 extending from a medical device handle 18 to a medical device implant 16. In some embodiments, the at least one actuator member 84 may include a plurality of actuator members 84, two actuator members 84, three actuator members 84, four actuator members 84, or another suitable or desired number of actuator members 84. For the purpose of illustration only, the medical device system 10 and/or the medical device implant 16 is shown with three actuator members 84.

In some embodiments, the first lumen may be lined with a low friction liner (e.g., a FEP liner). In some embodiments, disposed within the second lumen may be a pin release mandrel and/or at least one release pin, although dedicated release pins are not strictly necessary, and are not shown in the illustrated embodiment(s). In at least some embodiments, the second lumen may be lined with a hypotube liner. In some embodiments, the third lumen may be a guidewire lumen and/or the third lumen may also be lined with a hypotube liner. In some embodiments, the fourth lumen may be used to house a non-stretch wire or other reinforcing member. The exact form of the non-stretch wire or other reinforcing member may vary. In some embodiments, the non-stretch wire or other reinforcing member may take the form of a stainless steel braid. The non-stretch wire or other reinforcing member may optionally include a pair of longitudinally-extending aramid and/or para aramid strands (for example, KEVLAR®) disposed on opposite sides of the braid. In general, rather than being "disposed within" the fourth lumen, the non-stretch wire or other reinforcing member may be embedded within the fourth lumen. In addition, the non-stretch wire or other reinforcing member may extend to a position adjacent to the distal end portion but not fully to the distal end of the inner catheter 14. For example, a short distal segment of the fourth lumen may be filled in with polymer material adjacent to the distal end of the inner catheter 14.

In some embodiments, the inner catheter 14 may also include a guidewire extension tube that extends distally from the distal end portion. A nose cone may be attached to the guidewire extension tube. The nose cone may generally be designed to have an atraumatic shape. The nose cone may also include a ridge or ledge that is configured to abut the distal tip of the outer sheath 12 during delivery of the medical device implant 16.

FIGS. 2-3 illustrate some selected components of the medical device system 10 and/or the medical device implant 16 in the deployed (FIG. 2) and released (FIG. 3) configurations. For example, here it can be seen that the medical device implant 16 includes a plurality of valve leaflets 68 (e.g., bovine pericardial) which may be secured to a tubular anchor member or braid 70 that is reversibly actuatable between a "delivery" configuration, as in FIG. 1 for example, and a "deployed" configuration. In some embodiments, the anchor member or braid 70 may be substantially cylindrical in shape or configuration. In some embodiments, the anchor member or braid 70 may define a central longitudinal axis extending therethrough along a fluid flow path through the medical device implant 16. Other shapes and/or configurations are also contemplated. Some suitable but non-limiting materials for the anchor member or braid 70, for example metallic materials or polymeric materials, may be described below.

In some embodiments, the medical device implant 16 may include a plurality of locking mechanisms configured to secure the anchor member or braid 70 in the "deployed" configuration. In some embodiments, the at least one actuator member 84 may be configured to engage with the plurality of locking mechanisms and actuate the anchor member or braid 70 between the "delivery" configuration and the "deployed" configuration. In some embodiments, one actuator member 84 may correspond to, engage with, and/or actuate one locking mechanism. In some embodiments, one actuator member 84 may correspond to, engage with, and/or actuate more than one locking mechanism. Other configurations are also contemplated.

In some embodiments, the plurality of locking mechanisms may each comprise an axially movable post 72, for example at the commissure portions of the valve leaflets 68 (the post 72 may sometimes be referred to as a "commissure post", which may serve to secure the plurality of valve leaflets), and a buckle 76 fixedly attached to the anchor member or braid 70 (e.g., along an interior surface of the tubular anchor member or braid 70). In some embodiments, each of the plurality of valve leaflets 68 may be secured to the tubular anchor member or braid 70 at one post 72. In other words, in at least some embodiments, a medical device implant 16 may include a plurality of posts 72 and a corresponding plurality of buckles 76. Other configurations and correspondences are also contemplated. In the illustrated example(s), the medical device implant 16 includes three valve leaflets 68 secured to the tubular anchor member or braid 70 with three posts 72. The plurality of valve leaflets 68 may also be secured to the base or "distal end" of the tubular anchor member or braid 70. The plurality of posts 72, in turn, may be secured to the tubular anchor member or braid 70 (e.g., along an interior surface of the tubular anchor member or braid 70) with sutures or other suitable mechanisms.

For simplicity and clarity purposes, not all elements of the disclosed invention are necessarily shown in each figure or discussed in detail below. In some illustrative examples, only one of the plurality of actuator members 84, only one of the plurality of the posts 72, only one of the plurality of the buckles 76, etc., are shown and discussed (and/or the whole medical device implant 16 and/or the anchor member or braid 70 may not be shown to facilitate understanding of certain elements). However, it will be understood that the following discussion may apply equally to any and/or all of the components for which there are more than one within the medical device implant 16 (i.e., the plurality of actuator members 84, buckles 76, posts 72, etc.) and/or the medical device system 10.

In some embodiments, the post 72 may engage the buckle 76 in the "deployed" configuration, and consequently, in the "released" configuration. In some embodiments, the post 72 may be axially and/or longitudinally spaced apart from the buckle 76 in the "delivery" configuration. Some suitable but non-limiting materials for the post 72 and/or the buckle 76, for example metallic materials or polymeric materials, may be described below.

In some embodiments, a distal end of the axially movable post 72 may be secured and/or attached (i.e., fixedly attached, movably attached, removably attached, etc.) to a distal portion of the anchor member or braid 70, such as by a suture, a tether, adhesives, or other suitable element. In some embodiments, the post 72 may be movable relative to the anchor member or braid 70, and the buckle 76. In some embodiments, the post 72 may be axially or longitudinally movable relative to the anchor member or braid 70, and the buckle 76. In some embodiments, the buckle 76 may be fixedly attached to the anchor member or braid 70. Other embodiments are contemplated where the buckle 76 may be movably or removably attached to the anchor member or braid 70. In some embodiments, the post 72 may be fixedly attached to the anchor member or braid 70 and the buckle 76 may be fixedly attached to the anchor member or braid 70. In some embodiments, one of the post 72 and the buckle 76 may be fixedly attached to the anchor member or braid 70 and the other may be movably or removably attached to the anchor member or braid 70. In some embodiments, the post 72 may be movably or removably attached to the anchor member or braid 70 and the buckle 76 may be movably or removably attached to the anchor member or braid 70. In some embodiments, the post 72 may be secured or attached (i.e., fixedly attached, movably attached, removably attached, etc.) to a distal end of the anchor member or braid 70. In some embodiments, the buckle 76 may be fixed or attached to a proximal portion of the anchor member or braid 70. In some embodiments, the buckle 76 may be fixed or attached at or to a proximal end of the anchor member or braid 70.

In some embodiments, the medical device implant 16 may include one or more of the plurality of valve leaflets 68 secured to the anchor member or braid 70 at, adjacent to, and/or using (at least in part) individual, corresponding posts 72. In some embodiments, the plurality of valve leaflets 68 may also be secured to a base, or the distal end, of the anchor member or braid 70. As such, when the post 72 is pulled proximally to engage the buckle 76, as will be described herein, the distal end of the anchor member or braid 70 may also be pulled proximally relative to the buckle 76, thereby transitioning the anchor member or braid 70 and/or the medical device implant 16 from the "delivery" configuration toward the "deployed" configuration. In some embodiments, the plurality of valve leaflets 68 may be coupled and/or secured (i.e., to the post 72, to the anchor member or braid 70, and/or back to themselves) using one or more sutures, threads, wires, filaments, or other suitable elements. In some embodiments, the plurality of valve leaflets 68 may be coupled and/or secured (i.e., to the post 72, to the anchor member or braid 70, and/or back to themselves) using an adhesive, a bonding agent, or other suitable securing means. In some embodiments, the plurality of valve leaflets 68 may be coupled and/or secured (i.e., to the post 72, to the anchor member or braid 70, and/or back to themselves) using a fabric, a textile, or other thin flexible material.

In some embodiments, the anchor member or braid 70 may have a total of three buckles 76 and three posts 72 attached and/or secured thereto. Similarly, one actuator member 84 may be operatively associated with each post 72 and buckle 76, for a total of three actuator members 84 in the illustrated example(s). Other embodiments are contemplated where fewer or more buckles 76, posts 72, actuator members 84, etc. may be utilized. In some embodiments, a seal 74 may be disposed about the anchor member or braid 70 and, as the term suggests, may help to seal an exterior of the medical device implant 16 within and/or against an area of interest and/or a treatment location upon deployment, thereby preventing leakage around the medical device implant 16.

In some embodiments, attachment between the medical device implant 16 and the inner catheter 14 (and/or the outer sheath 12) may be effected through the use of a coupler 78. The coupler 78 may generally include a cylindrical base (not shown) that may be disposed about, attached to, and/or extending from a distal end of the inner catheter 14 (and/or the outer sheath 12). Projecting distally from the base is a plurality of fingers (e.g., two fingers, three fingers, four fingers, etc.) that are each configured to engage with the medical device implant 16 at the buckles 76 (for example, at a proximal end of the buckles 76), with the plurality of actuator members 84 extending therethrough and engaging the posts 72. A collar 80 may be disposed about each of the fingers of the coupler 78 to further assist in holding together the fingers and the buckles 76. A guide 82 may be disposed over each of the fingers proximal of the collar 80 and may serve to keep the fingers of the coupler 78 associated with the actuator members 84 extending adjacent to (and axially slidable relative to) the fingers of the coupler 78. Finally, in some embodiments, a pin release assembly 86 may be a linking structure that keeps the posts 72, the buckles 76, and the actuator members 84 associated with one another. The pin release assembly 86 may include a plurality of release pins 88 that may be joined together (e.g. via a coiled connection 90) and held to a pin release mandrel 92 (with a ferrule 94, for example). As mentioned above, the pin release assembly 86 may not be present in all embodiments of the medical device implant 16, and in at least some embodiments, may utilize one or more of various "pinless" release and/or locking mechanisms. Other suitable configurations are also contemplated. Some suitable but non-limiting materials for the coupler 78, the fingers, the collars 80, the guides 82, and/or the pin release assembly, for example metallic materials or polymeric materials, may be described below.

During delivery, the medical device implant 16 may be secured at the distal end of the inner catheter 14 by virtue of the association of the fingers of the coupler 78 being coupled with a projecting proximal end of the buckles 76 (and being held in place with the collar 80 disposed over the connection) and by virtue of the actuator members 84 and the posts 72 being operatively secured together. When the medical device implant 16 is advanced within the anatomy to the desired location, the outer sheath 12 may be withdrawn (e.g., moved proximally relative to the inner catheter 14 and/or the medical device implant 16) to expose the medical device implant 16. Then, the actuator members 84 can be used to translate and "lock" the medical device implant 16 in the "deployed" configuration by proximally retracting the actuator members 84 to pull the posts 72 into engagement with the buckles 76. Finally, in some embodiments, the release pins 88 can be removed, thereby uncoupling the actuator members 84 from the posts 72, which allows the medical device implant 16 to be released from the medical device system 10 and deployed in the anatomy. In some embodiments, the release pins 88 and/or the pin release assembly 86 may not be present, and other and/or alternative means of releasing the medical device implant 16 may be utilized, such as a displacement-based or distance-based means of releasing the medical device implant 16.

Figure 4:
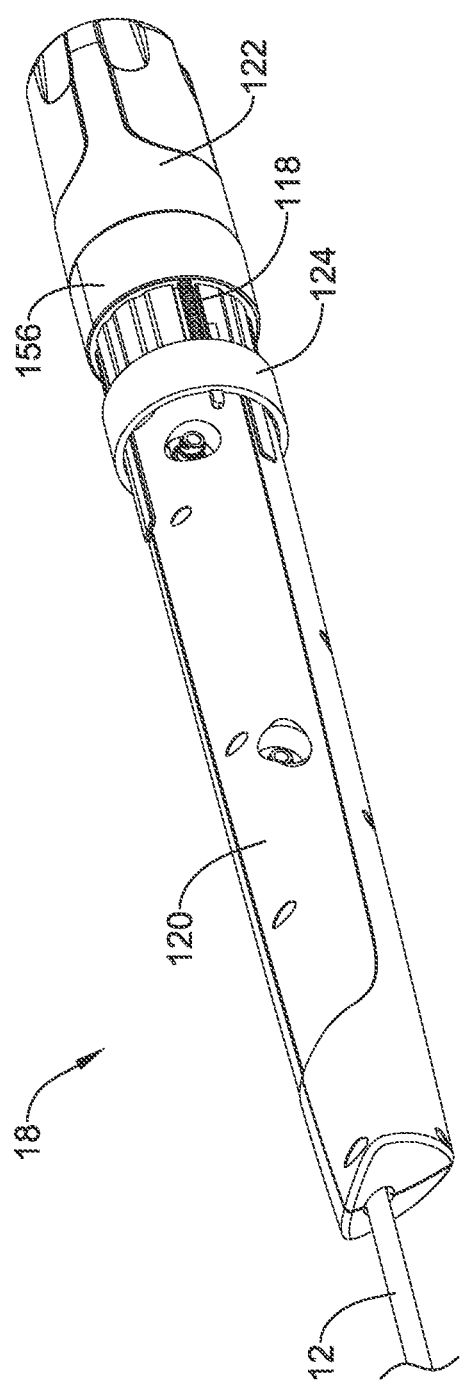
FIG. 4 illustrates an example medical device handle.

FIG. 4 illustrates an example medical device handle 18. Here it can be seen that the medical device handle 18 may include an elongated handle housing 120. A rotatable control knob 122 may be disposed about the elongated handle housing 120 (e.g., at a proximal end of the elongated handle housing 120) and may be used to actuate and/or move one or more of the components of the medical device system 10 (e.g., the outer sheath 12, the actuator members 84, etc.). In some embodiments, the elongated handle housing 120 may include an axial translation mechanism disposed therein and operatively connected to the rotatable control knob 122. In some embodiments, the axial translation mechanism may convert rotational motion of the rotatable control knob 122 into axial translation of a carriage element disposed within the elongated handle housing 120, as will become apparent from the discussion below.

In some embodiments, a rotatable collar 156 may be disposed about the elongated handle housing 120. In some embodiments, the rotatable control knob 122 may be disposed about a proximal portion 180 of the rotatable collar 156. In some embodiments, a release ring 124 may also be slidably disposed about the elongated handle housing 120 and/or a distal portion 182 of the rotatable collar 156. In some embodiments, the release ring 124 may be rotatably fixed to and/or relative to the rotatable collar 156. In other words, in some embodiments, the release ring 124 and the rotatable collar 156 may rotate together simultaneously, and/or may not rotate independently of each other. In some embodiments, the release ring 124 may be biased distally toward a first position relative to the rotatable collar 156 by a plurality of compression springs 118 disposed therebetween. In some embodiments, the medical device handle 18 may also include one or more apertures through the elongated handle housing 120 and/or flush ports accessible therethrough that can be used to flush certain elements (e.g., components, lumens, etc.) of the medical device system 10 as described herein.

As will be discussed in more detail below, in some embodiments, the release ring 124 may slidably translate proximally to a second position relative to the rotatable collar 156 to release an interlock feature and permit the rotatable collar 156 to rotate about and/or relative to the elongated handle housing 120 to place the medical device system 10 in condition to translate the medical device implant 16 from the "deployed" configuration to the "released" configuration. In some embodiments, the rotatable collar 156 and/or the release ring 124 may be rotated about and/or relative to the elongated handle housing 120 to move one or more components of the medical device system 10 (e.g., the actuator members 84, the pin release mandrel 92, etc.).

Figure 5:
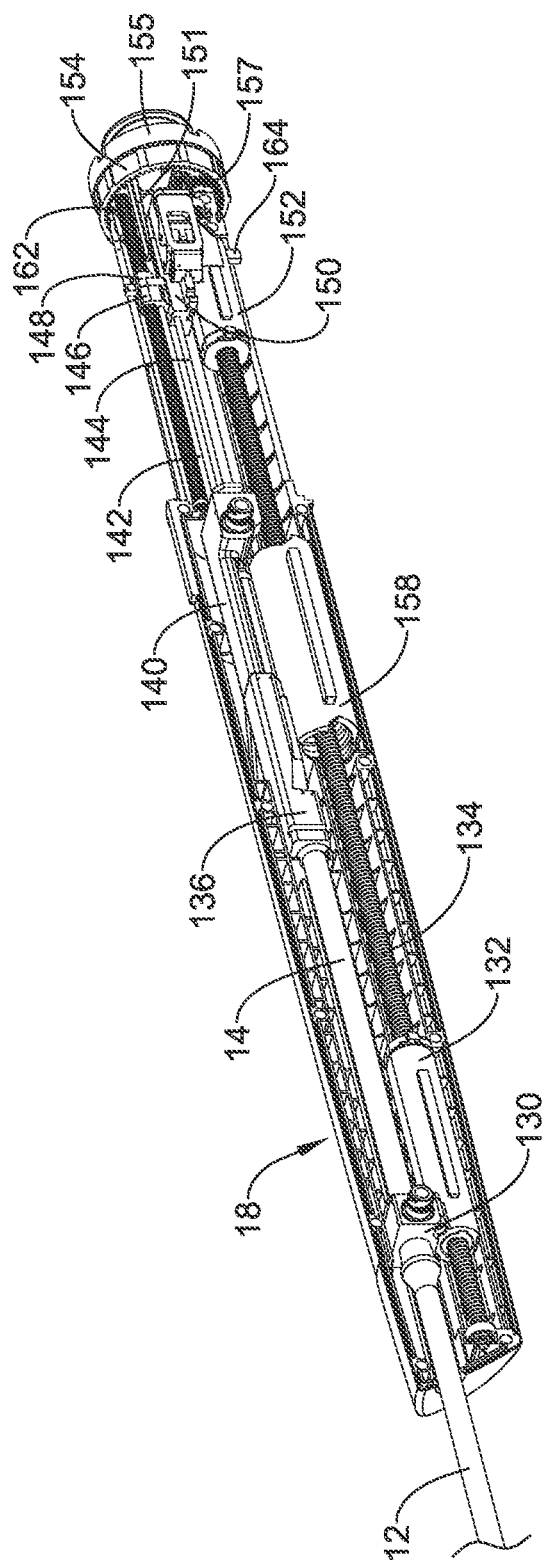
FIG. 5 is a partial cut-away view illustrating some of the interior components of the example medical device handle of FIG. 4.

FIG. 5 is a partial cut-away view of the medical device handle 18 with a portion of the elongated handle housing 120 removed, exposing at least some of the interior components. For clarity, not all elements of the medical device handle 18 are shown. In some embodiments, the outer sheath 12 may be attached to a sheath adapter 130. The sheath adapter 130 may be attached to a sheath carriage 132, which may be threaded onto a lead screw 134. In some embodiments, a distal flush port may be disposed on the sheath adapter 130. In general, the distal flush port may provide fluid access to the interior or lumen of the outer sheath 12 (e.g., access to space between the inner catheter 14 and the outer sheath 12) so that a clinician can flush fluid through the lumen of the outer sheath 12 to remove any unwanted materials (e.g., air, fluid, contaminants, etc.) therein prior to use of the medical device system 10. In at least some embodiments, the distal flush port may have a luer type connector (e.g., a one-way luer connector) that allows a device such as a syringe with a corresponding connector to be attached thereto for flushing.

Extending through and proximally from the sheath adapter 130 is the inner catheter 14. A proximal end of the inner catheter 14 may be attached (e.g., fixedly attached) to a diverter 136. The diverter 136 may be attached (e.g., fixedly attached) to a support body 140. In general, the diverter 136 and/or the support body 140 may have one or more passageways formed therein. While not explicitly shown, in some embodiments, the plurality of actuator members 84 and/or a pin release mandrel 92 may extend through respective passageways. Alternatively, the proximal ends of the plurality of actuator members 84 and/or a pin release mandrel 92 may each be attached to a shaft or hypotube (e.g., solid in cross-section, tubular, etc.), and each shaft or hypotube may extend through the one or more passageways. For example, a first shaft or hypotube 142 and a second shaft or hypotube 144 may extend through the passageways in diverter 136, and in some embodiments, the first shaft or hypotube 142 extends through a first passageway and the second shaft or hypotube 144 extends through a second passageway that is separate or distinct from the first passageway. In at least some embodiments, the first shaft or hypotube 142 may be attached to the pin release mandrel 92. In at least some embodiments, the second shaft or hypotube 144 may be attached to the plurality of actuator members 84. It should be noted that at in least some embodiments of the medical device system 10, three actuator members 84 are utilized. In these embodiments, the three actuator members 84 may come together (e.g., may be brought into contact with one another or otherwise brought into relatively close proximity with one another) adjacent to the distal end of the inner catheter 14 and enter the first lumen of the inner catheter 14. At one or more positions along their length, the plurality of actuator members 84 may be attached to one another. For example, in some embodiments, the plurality of actuator members 84 may be welded together about 10.16 cm (about 4.00 inches) from their distal ends. In some embodiments, the plurality of actuator members 84 may be welded together proximate their proximal ends in addition to or instead of the distal weld. Proximally thereafter, the plurality of actuator members 84 may extend to and/or may be fixedly attached to the second shaft or hypotube 144.

In some embodiments, a hypotube (e.g., a hypotube liner disposed along the guidewire lumen) may extend through the diverter 136 within a passageway therein and then be "diverted" around a portion of the diverter 136 and the support body 140, and ultimately be extended to a position at the proximal end of the medical device handle 18 so as to provide a user access to the guidewire lumen. A proximal flush port may be disposed on the support body 140 that can be used to flush the lumen(s) of the inner catheter 14 and, for example, may function similarly to the distal flush port.

At their respective proximal ends, the first shaft or hypotube 142 may be secured to a slider 146 and the second shaft or hypotube 144 may be secured to a force limiter body 150. The connections between the various components may include a number of different types of connections including mechanical bonding (e.g., pinning, threading, interference fit, etc.), adhesive bonding, thermal bonding, etc. In some embodiments, the slider 146 may be slidable relative to the force limiter body 150. In some embodiments, the slider 146 may be selectively locked to the force limiter body 150, thereby preventing relative movement between the slider 146 and the force limiter body 150. In some embodiments, the force limiter body 150 may be secured to an actuator member carriage 152, which may be threaded onto the lead screw 134. Thus, movement of the lead screw 134 can cause movement of the actuator member carriage 152 and the force limiter body 150 and thus, plurality of actuator members 84 (via the second shaft or hypotube 144). Some additional details regarding this motion can be found herein.

In general, the force limiter body 150 may form or define a stop point that provides tactile feedback (e.g., resistance to further rotation of the rotatable control knob 122) to the user indicating that the plurality of actuator members 84 have been retracted proximally a sufficient distance to secure the plurality of locking mechanisms (e.g., engage and/or lock the posts 72 with the buckles 76). To verify proper locking, a clinician may use an appropriate visualization technique to visualize proper locking (e.g., the relative positioning of the posts 72 and the buckles 76). In some embodiments, a chock 148 may be positioned adjacent to the slider 146 to selectively lock the slider 146 to the force limiter body 150. In order to allow the pin release mandrel 92 to be proximally retracted to pull the release pins 88, the chock 148 can be rotated or otherwise moved to a secondary position or configuration. When in this secondary position or configuration, the chock 148 no longer forms a barrier to further movement of, for example, the slider 146 and the pin release mandrel 92. Accordingly, with the chock 148 no longer acting as an impediment, the slider 146 and the pin release mandrel 92 can be proximally retracted to facilitate deployment of the medical device implant 16 by allowing the release pins 88 to be pulled. In some embodiments, such as those utilizing pinless release and/or locking mechanisms for example, the slider 146, the chock 148, and other associated components may be omitted.

In some embodiments, the medical device handle 18 may include a rotatable ring 155 with internal teeth that are configured to engage with teeth on a gear 157 coupled to the lead screw 134. The rotatable ring 155 is coupled to the rotatable control knob 122 so that rotation of the rotatable control knob 122 results in analogous motion of the rotatable ring 155 and thus the lead screw 134.

The medical device handle 18 may be generally configured for coordinated movement of multiple structures of the medical device system 10. In some embodiments, the medical device handle 18 and/or the elongated handle housing 120 may include an axial translation mechanism disposed therein and operatively connected to the rotatable control knob 122. In some embodiments, the axial translation mechanism may convert rotational motion of the rotatable control knob 122 into axial translation of a carriage element (e.g., the actuator member carriage 152, the sheath carriage 132, etc.—which terms may be used interchangeably with the term "carriage element" throughout the disclosure) disposed within the medical device handle 18 and/or the elongated handle housing 120. For example, the medical device handle 18 may be configured to allow a user to move the outer sheath 12 (e.g., relative to the inner catheter 14), move the plurality of actuator members 84, and in some embodiments, move a pin release mandrel 92. Moreover, the medical device handle 18 may be configured so that the appropriate structure can be moved at the appropriate time during the intervention so that the medical device implant 16 can be delivered in an efficient manner. In some embodiments, the medical device handle 18 may be configured to allow a user to sequentially move the outer sheath 12, move the plurality of actuator members 84, and/or move the pin release mandrel 92.

Figure 6:
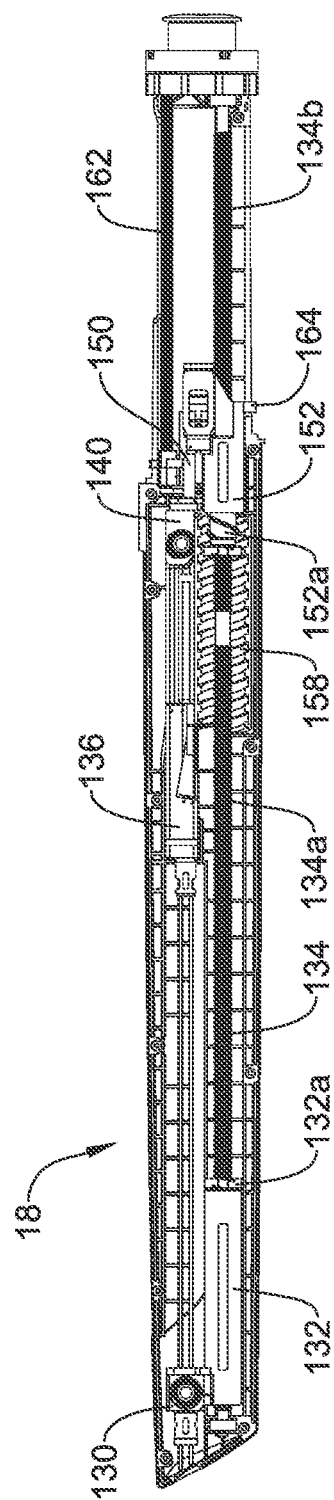
FIGS. 6-8 illustrate an example of coordinated movement of some components within the example medical device handle of FIG. 4.
Figure 7:
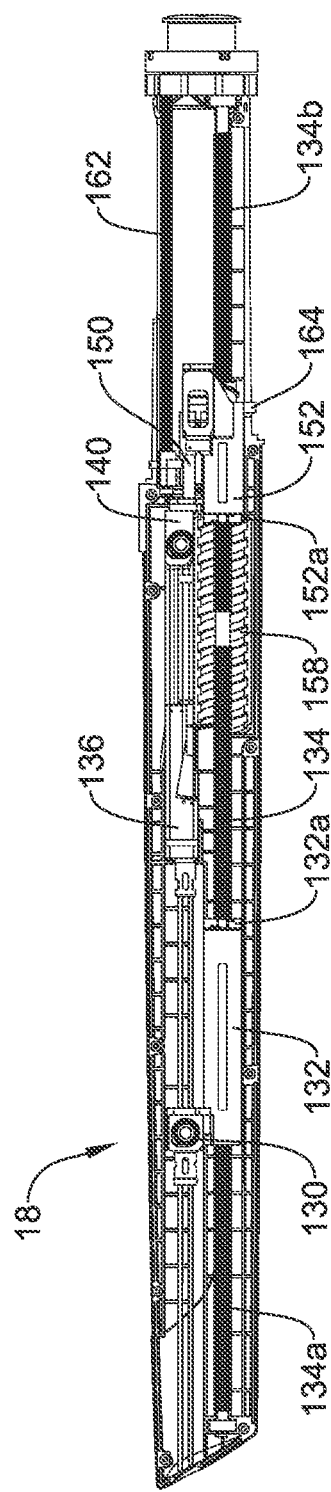
Figure 8:
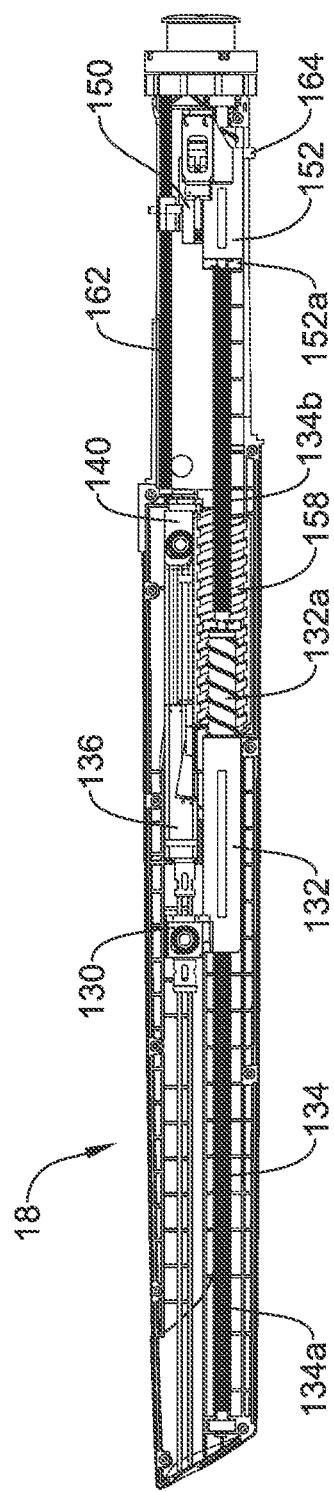

To help facilitate the coordinated movement, the medical device handle 18 and/or the elongated handle housing 120 may include a lost motion barrel 158 formed therein. In some embodiments, the lost motion barrel 158 may be configured to engage the sheath carriage 132, the actuator member carriage 152, and/or the lead screw 134 at different times during the intervention to stop motion (e.g., create "lost motion" of the appropriate carriage). FIGS. 6-8 illustrate some of the coordinated motion that may be achieved by the medical device handle 18. It should be noted that some elements of the medical device system 10 are not shown in FIGS. 6-8 for clarity.

FIG. 6 illustrates a first position of the medical device handle 18 wherein the outer sheath 12 may be extended distally relative to the inner catheter 14 (and/or the medical device handle 18) so as to fully sheath (e.g., contain) the medical device implant 16 within the lumen of the outer sheath 12 (e.g., the medical device implant 16 is in the "delivery" configuration). While in the first position, the sheath carriage 132 and/or the proximal end of the outer sheath 12 may be positioned adjacent to the distal end of the medical device handle 18. In addition, an actuator carriage screw 152a associated with the actuator member carriage 152 may extend distally from the actuator member carriage 152 and be positioned within the lost motion barrel 158. Upon rotation of the rotatable control knob 122 (e.g., in a first or clockwise direction), the lead screw 134 begins to rotate. Rotation of the lead screw 134 causes the sheath carriage 132 to move along the lead screw 134 in the proximal direction, as seen in FIG. 7 for example, resulting in proximal movement of the outer sheath 12 relative to the inner catheter 14 and/or the medical device handle 18 (e.g., the elongated handle housing 120) thereby "unsheathing" the medical device implant 16. This initial rotation of the lead screw 134 also causes the actuator carriage screw 152a to rotate. This may be because, for example, a projection (not shown) on the actuator carriage screw 152a may be engaged with a helical thread disposed along an interior of the lost motion barrel 158. However, because the actuator carriage screw 152a is spaced from the actuator member carriage 152, it does not exert a force onto the actuator member carriage 152. Thus, initial rotation of the rotatable control knob 122 does not result in movement of the actuator member carriage 152 and, instead, only results in translation of the sheath carriage 132 and rotation (and translation) of the actuator carriage screw 152a.

Eventually, the actuator carriage screw 152a (e.g., the projection extending therefrom) reaches an essentially linear thread or pathway formed at a proximal end of the lost motion barrel 158. The linear thread allows the actuator carriage screw 152a to stop rotating and instead translate proximally along the lead screw 134 to a position where the actuator carriage screw 152a contacts (e.g., is threaded within and abuts against) a distal end of the actuator member carriage 152, as seen in FIG. 7. In doing so, continued rotation of the rotatable control knob 122 results in the actuator carriage screw 152a moving the actuator member carriage 152 proximally within the elongated handle housing 120 as seen in FIG. 8. Accordingly, further rotation of the lead screw 134 not only causes the sheath carriage 132 to move proximally but also causes the actuator member carriage 152 to move proximally as shown in FIGS. 7-8.

When the sheath carriage 132 reaches the lost motion barrel 158, the sheath carriage 132 stops translating proximally and a sheath carriage screw 132a of the sheath carriage 132 engages the lost motion barrel 158 and moves proximally as shown in FIG. 8. This may occur in a manner similar to how the actuator carriage screw 152a threads and unthreads with the helical thread formed along the lost motion barrel 158. For example, while the sheath carriage 132 is translating, the sheath carriage screw 132a may follow an essentially linear thread or pathway formed along or adjacent to (e.g., distal of) the lost motion barrel 158. Upon reaching the lost motion barrel 158, the sheath carriage screw 132a (e.g., a projection formed thereon) may shift into engagement with the helical thread within the lost motion barrel 158 and rotate. This rotation "unthreads" the sheath carriage screw 132a from the sheath carriage 132. Accordingly, additional rotation of the rotatable control knob 122 and/or the lead screw 134 results in continued proximal movement of the actuator member carriage 152 while motion of the sheath carriage 132 ceases.

In at least some embodiments, the lead screw 134 may have a plurality of portions, for example a first portion 134a and a second portion 134b, with each having a different thread pitch. This may allow the sheath carriage 132 and the actuator member carriage 152 to travel at different rates along the lead screw 134. For example, the pitch of the lead screw 134 along the first portion 134a which the sheath carriage 132 translates may be generally more spaced or slanted than along the second portion 134b. Accordingly, the coordinated movement of the sheath carriage 132 and the actuator member carriage 152 may be configured so that the sheath carriage 132 translates along the lead screw 134 at a greater rate than the actuator member carriage 152. Other configurations are contemplated where the above-mentioned configuration is reversed as well as further configurations where the pitch of the lead screw 134 is essentially constant or includes a number of different pitch regions. Sufficient proximal retraction of the actuator member carriage 152 may result in the plurality of actuator members 84 being sufficiently retracted so that the posts 72 can engage and lock with the buckles 76, thereby transitioning the medical device implant 16 from the "delivery" configuration to the "deployed" configuration.

In some embodiments, when the clinician is satisfied that locking is complete (e.g., after verification via an appropriate visualization technique), the clinician may proximally retract the pin release mandrel 92 in order to pull the release pins 88, and withdraw the plurality of actuator members 84 from the plurality of locking mechanisms and/or the medical device implant 16 to release the medical device implant 16. In some embodiments, the actuator member carriage 152 may include a laterally-extending protrusion or flag member 164. In general, the laterally-extending protrusion or flag member 164 may be designed as a feature that can prevent the rotatable collar 156 from being rotated earlier than desired (and, thus, prevent the release pins 88 from being pulled earlier than desired in embodiments including the release pins 88). For example, the laterally-extending protrusion or flag member 164 may be positioned within and follow a first internally-facing longitudinal slot 186 proximally along an interior surface of the rotatable collar 156. While positioned within the first internally-facing longitudinal slot 186, the laterally-extending protrusion or flag member 164 essentially forms a physical barrier that prevents the rotatable collar 156 from rotating relative to the elongated handle housing 120. When the actuator member carriage 152 is translated proximally to the back of the elongated handle housing 120 and the force limiter body 150 reaches the stop point (e.g., when plurality of actuator members 84 are proximally retracted so as to engage and/or lock the posts 72 with the buckles 76), the laterally-extending protrusion or flag member 164 may exit the first internally-facing longitudinal slot 186 in the rotatable collar 156. Accordingly, the laterally-extending protrusion or flag member 164 no longer impedes rotation of the rotatable collar 156 and, as such, the rotatable collar 156 can now be rotated to pull the release pins 88. The rotatable collar 156, via the ring 154, may be associated with a gear (not shown) engaged with a secondary screw 162. Notches at a proximal end of the rotatable collar 156 engage protrusions on the ring 154 such that rotation of the rotatable collar 156 causes corresponding rotation of the ring 154 and thus the secondary screw 162. The initial rotation of the rotatable collar 156 is sufficient to rotate the chock 148 (e.g., via a mechanical interaction between the rotatable collar 156 and the chock 148 that causes the chock 148 to shift) from a first configuration where the slider 146 (and, thus, the pin release mandrel 92) is selectively locked to the force limiter body 150, to a secondary configuration, which permits the slider 146 to translate along the secondary screw 162 as the secondary screw 162 rotates, to proximally retract and pull the release pins 88 (e.g., via the pin release mandrel 92). The chock 148 in the first configuration may engage a ridge along a top portion of the force limiter body 150 which forms a physical barrier that prevents proximal translation of the slider 146 relative to the force limiter body 150. When the rotatable collar 156 is rotated to shift the chock 148 into the secondary configuration, the slider 146 can translate proximally within a groove disposed in the top portion of the force limiter body 150, as the rotatable collar 156 is rotated about the elongated handle housing 120 to pull the release pins 88. Once the release pins 88 have been removed, the rotatable control knob 122 may be further rotated to withdrawn the plurality of actuator members 84 from the medical device implant 16, thereby deploying the implant at the target site (area of interest) in the "released" configuration. In some embodiments lacking the release pins 88, after rotating the rotatable collar 156, further rotation of the rotatable control knob 122 is no longer impeded, and additional rotation of the rotatable control knob 122 withdraws the plurality of actuator members 84 from the plurality of locking mechanisms and/or the medical device implant 16 to deploy the medical device implant 16 in the "released" configuration. In some embodiments, actuation and release features and/or procedures may very slightly depending upon the configuration of the medical device handle 18. Selected examples related to some embodiments may be described in more detail below.

Following deployment of the medical device implant 16, the rotatable control knob 122 may be rotated to move the sheath carriage 132 distally within the elongated handle housing 120, thereby moving the outer sheath 12 distally relative to the inner catheter 14 and the coupler 78 so as to cover or re-sheath the elements of the medical device system 10 disposed at the distal end. The medical device system 10 may then be removed from the patient's anatomy.

Figure 9:
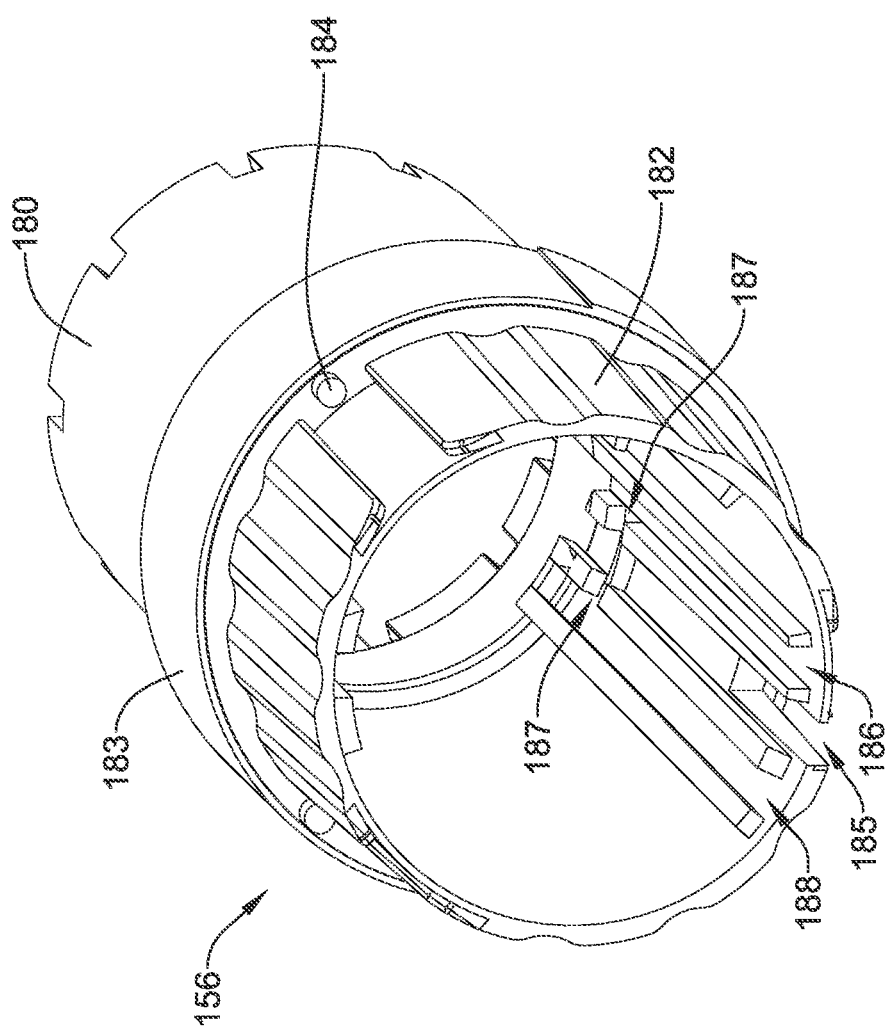
FIG. 9 is a perspective view of an example collar of the example medical device handle of FIG. 4.

FIG. 9 illustrates an example rotatable collar 156. In some embodiments, the rotatable collar 156 may include a proximal portion 180 and a distal portion 182. In some embodiments, the proximal portion 180 may include a plurality of notches at a proximal end of the rotatable collar 156, the plurality of notches being configured to engage with the ring 154, as discussed above. In some embodiments, the rotatable control knob 122 may be disposed about and/or over the proximal portion 180 of the rotatable collar 156. In some embodiments, a release ring 124 may be slidably disposed about and/or over the distal portion 182 of the rotatable collar 156. In some embodiments, a middle portion 183 of the rotatable collar 156 may be disposed and/or extend between the proximal portion 180 and the distal portion 182. In some embodiments, the middle portion 183 may extend radially outward farther than the proximal portion 180 and/or the distal portion 182, and/or may form a radially extending ridge along an outer surface of the rotatable collar 156. The middle portion 183 and/or the radially extending ridge may include a proximal face and a distal face. In some embodiments, a plurality of first protrusions 184 may extend distally from the distal face of the middle portion 183 and/or the radially extending ridge. In some embodiments, the plurality of first protrusions 184 may include three protrusions. In some embodiments, the plurality of first protrusions 184 may include two protrusions, four protrusions, five protrusions, or another suitable number of protrusions.

In some embodiments, the rotatable collar 156 may include one or more slots disposed along an inner surface of the rotatable collar 156. In some embodiments, the rotatable collar 156 may include a first internally-facing longitudinal slot 186 extending less than a full length of the rotatable collar. In some embodiments, the actuator member carriage 152 may include a laterally-extending protrusion or flag member 164 configured to engage with the first internally-facing longitudinal slot 186 (as shown schematically in phantom in FIG. 12). In general, the laterally-extending protrusion or flag member 164 may be designed as a feature that can prevent the rotatable collar 156 from being rotated earlier than desired. For example, the laterally-extending protrusion or flag member 164 may be positioned within and follow the first internally-facing longitudinal slot 186 along an inner surface of the rotatable collar 156.

In some embodiments, an internally-facing circumferentially-oriented slot and/or a plurality of notches 187 operatively connects the first internally-facing longitudinal slot 186 with a second internally-facing longitudinal slot 188. In some embodiments, the internally-facing circumferentially-oriented slot and/or the plurality of notches 187 extends between the first internally-facing longitudinal slot 186 and the second internally-facing longitudinal slot 188. In some embodiments, the second internally-facing longitudinal slot 188 may extend both proximally and distally from the internally-facing circumferentially-oriented slot and/or the plurality of notches 187. In some embodiments, the first internally-facing longitudinal slot 186 and the second internally-facing longitudinal slot 188 may be oriented substantially parallel to a central longitudinal axis of the rotatable collar 156 and/or to each other. In some embodiments, the rotatable collar 156 may include a longitudinally-oriented cut-out 185 extending through the distal portion 182. In some embodiments, the longitudinally-oriented cut-out 185 may extend proximally from a distal end of the distal portion 182 and/or the rotatable collar 156. In some embodiments, the longitudinally-oriented cut-out 185 may be circumferentially disposed between the first internally-facing longitudinal slot 186 and the second internally-facing longitudinal slot 188.

Figure 10:
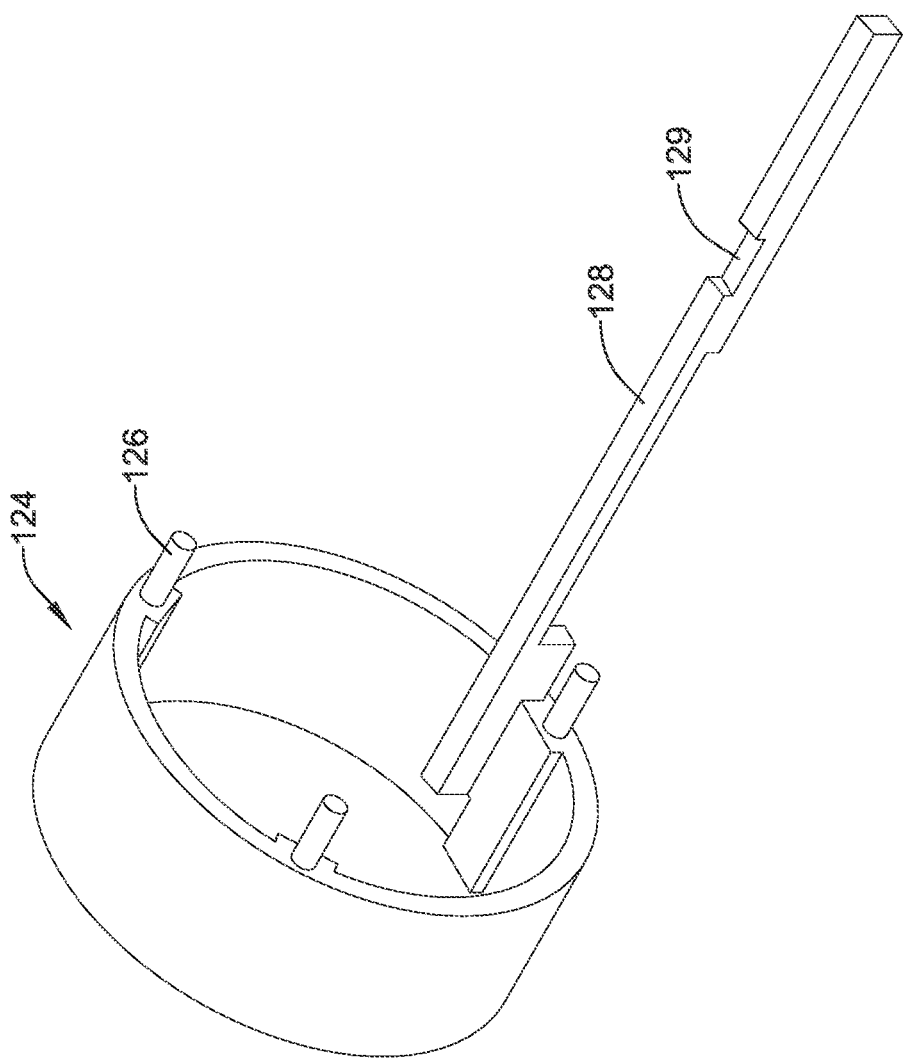
FIG. 10 is a perspective view of an example release ring of the example medical device handle of FIG. 4.

In some embodiments, the medical device handle 18 may include a release ring 124, as seen in FIG. 10 for example, disposed about and/or engaged with the distal portion 182 of the rotatable collar 156. In some embodiments, the release ring 124 may include an arm 128 extending longitudinally and/or proximally within the rotatable collar 156. In some embodiments, the arm 128 may be configured to engage with the longitudinally-oriented cut-out 185 of the rotatable collar 156. In some embodiments, the release ring 124 and/or the arm 128 may be slidable and/or axially translatable from a first position at and/or adjacent a distal end of the rotatable collar 156 to a second position proximal of the first position. In some embodiments, the arm 128 may include a notch 129 facing radially inward toward the central longitudinal axis of the rotatable collar 156. In at least some embodiments, the medical device handle 18 may include a plurality of compression springs 118 disposed between the release ring 124 and the middle portion 183 and/or the radially-extending ridge of the rotatable collar 156. In some embodiments, the release ring 124 may include a plurality of second protrusions 126 extending proximally from the release ring 124. In some embodiments, the plurality of second protrusions 126 may include three protrusions. In some embodiments, the plurality of second protrusions 126 may include two protrusions, four protrusions, five protrusions, or another suitable number of protrusions. In general, the plurality of first protrusions 184 and the plurality of second protrusions 126 may each include the same number of protrusions. However, other configurations are also contemplated.

Figure 11:
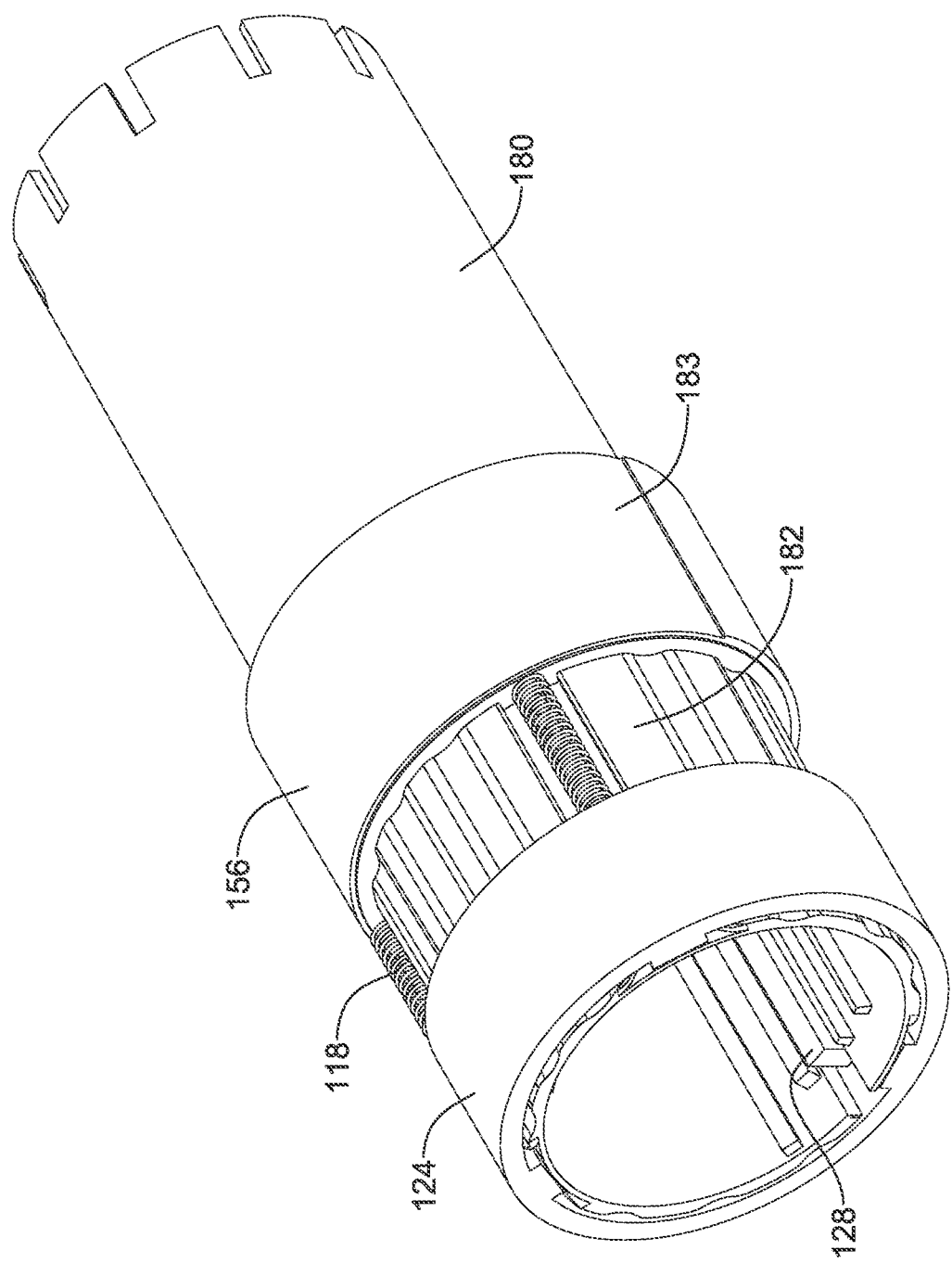
FIGS. 11-13 illustrate an example of interaction between the example collar of FIG. 9 and the example release ring of FIG. 10.

As seen in FIG. 11 for example, in some embodiments, the plurality of second protrusions 126 of the release ring 124 may be axially aligned with and/or coaxial with the plurality of first protrusions 184 of the rotatable collar 156. In some embodiments, each of the plurality of second protrusions 126 may be configured to receive one of the plurality of compression springs 118 thereon. Similarly, each of the plurality of first protrusions 184 of the rotatable collar 156 may be configured to receive one of the plurality of compression springs 118 thereon. As such, the plurality of compression springs 118 may be captured and/or trapped between the rotatable collar 156 and the release ring 124. In some embodiments, the plurality of compression springs 118 biases the release ring 124 and/or the arm 128 distally relative to the rotatable collar 156. In the illustrated example(s), three compression springs 118 are shown, but other configurations, including additional or fewer compression springs 118 (e.g., one two, four, five, six, etc.), are also contemplated. For example, in some embodiments, one compression spring may encircle the distal portion 182 of the rotatable collar 156 and extend between the release ring 124 and the middle portion and/or the radially-extending ridge of the rotatable collar 156.

Figure 12:
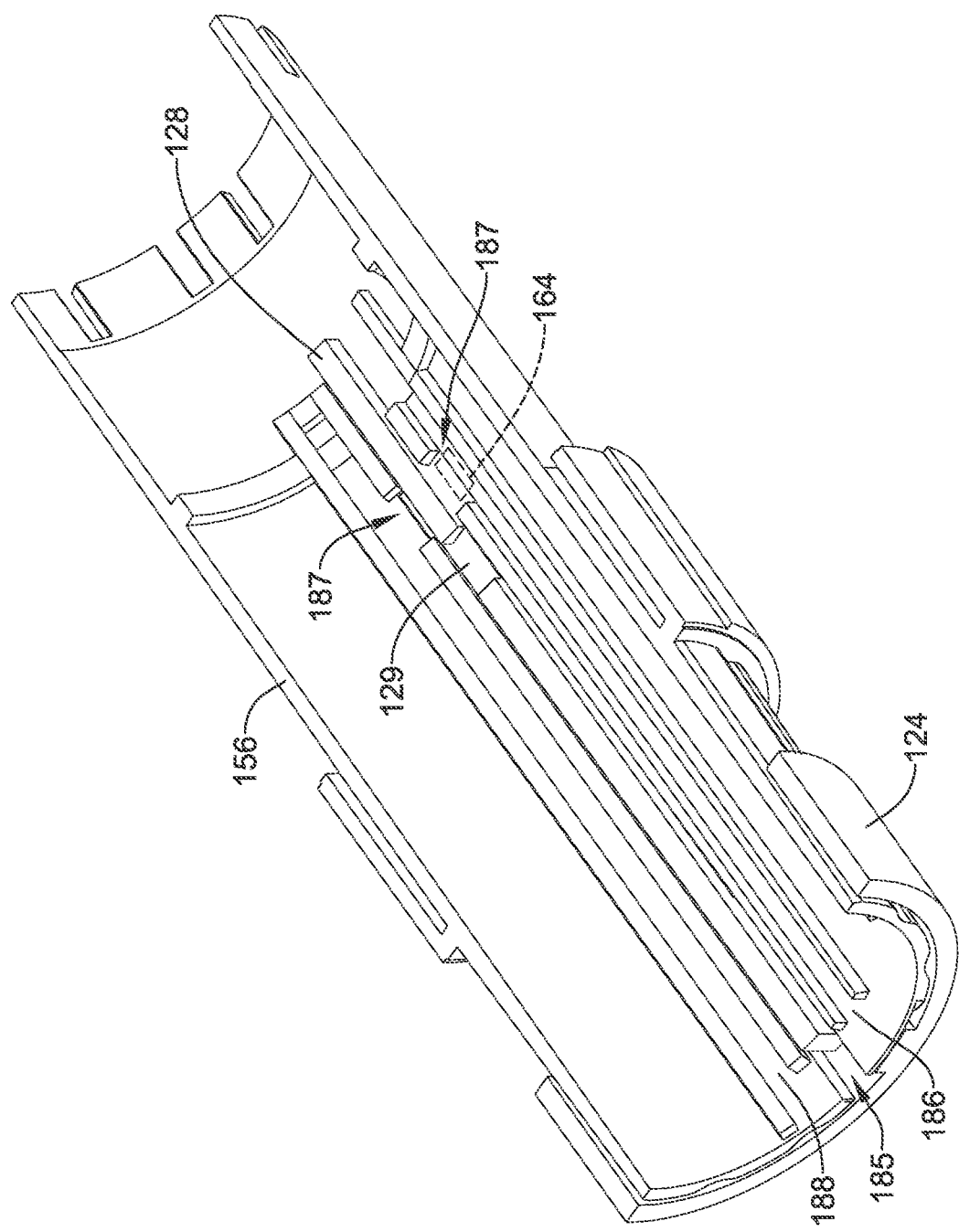
Figure 13:
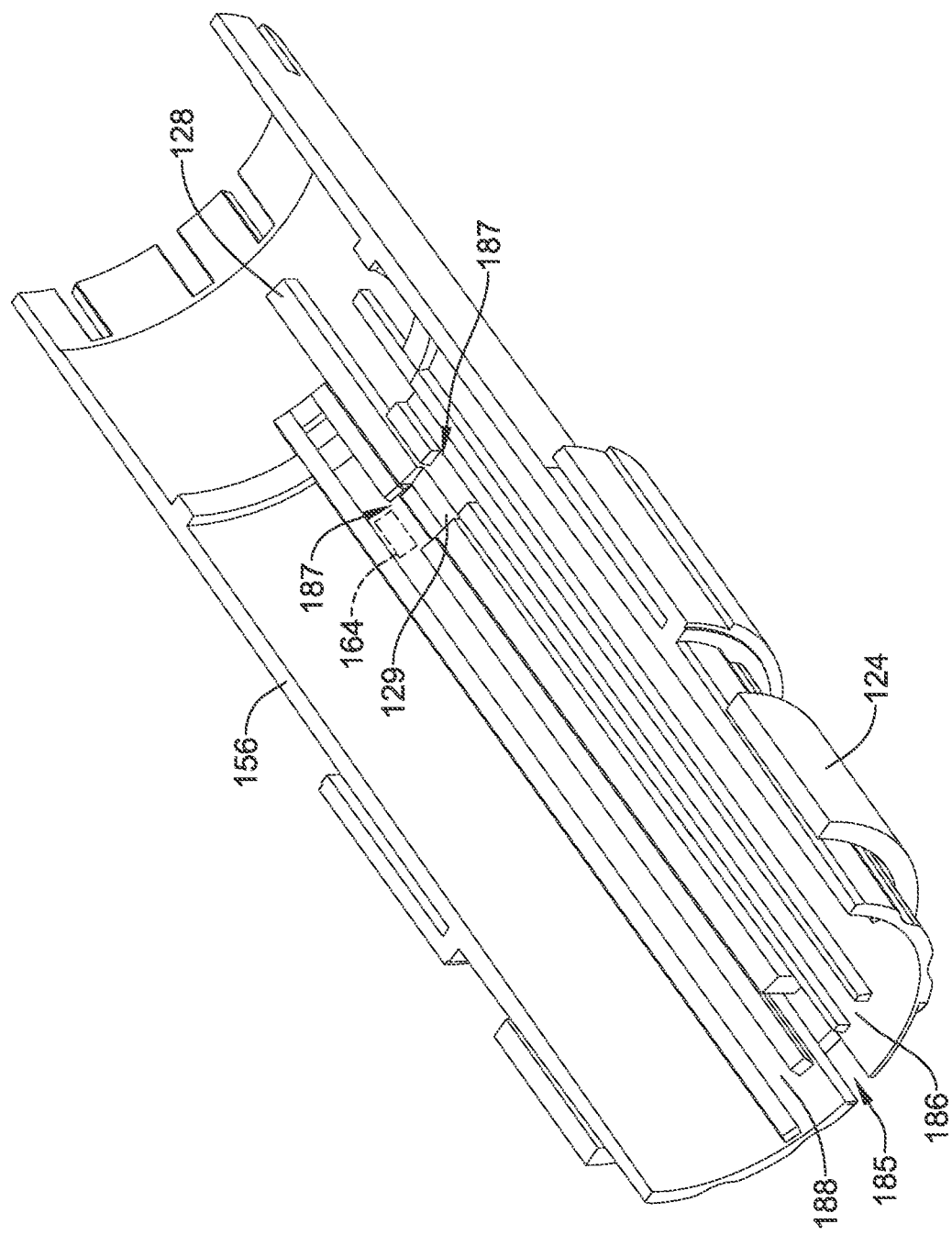

In some embodiments, and as seen in FIG. 12 for example, the arm 128 may physically and/or mechanically prevent the rotatable collar 156 from rotating about the elongated handle housing 120 and/or may prevent the laterally-extending protrusion or flag member 164 (shown schematically in phantom) from circumferentially translating from the first internally-facing longitudinal slot 186 when the release ring 124 is in the first position. In some embodiments, proximal translation of the release ring 124 relative to the rotatable collar 156 and/or the elongated handle housing 120 may shift the release ring 124 from the first position to the second position. In the second position, the notch 129 of the arm 128 and/or the release ring 124 may align with the internally-facing circumferentially-oriented slot and/or the plurality of notches 187 of the rotatable collar 156, and thus may permit the laterally-extending protrusion or flag member 164 to access the internally-facing circumferentially-oriented slot from the first internally-facing longitudinal slot 186 and thus translate toward and/or into the second internally-facing longitudinal slot 188 by rotating the rotatable collar 156 about the elongated handle housing 120, as seen in FIG. 13 for example. After the laterally-extending protrusion or flag member 164 accesses and/or engages the second internally-facing longitudinal slot 188, the rotatable control knob 122 may be further rotated to withdraw the plurality of actuator members 84 from the plurality of locking mechanisms and/or the medical device implant 16, similar to what is described above. In at least some embodiments, a medical device handle 18 including the release ring 124 and/or the arm 128 may lack and/or not include the release pins 88 and/or the pin release mandrel 92 and the associated actuation components and/or means within the medical device handle 18 (e.g., may use "pinless" release and/or locking mechanisms). However, in some embodiments, the release ring 124 and the rotatable collar 156 may cooperate to rotate together to pull the release pins 88 and release the medical device implant 16 as described above.

After releasing the medical device implant 16, the rotatable control knob 122 may be rotated in the second, opposite direction to actuate and/or rotate the lead screw 134. Actuating and/or rotating the lead screw 134 may actuate and/or translate the actuator member carriage 152 and the laterally-extending protrusion of flag member 164 distally within the second internally-facing longitudinal slot 188, while leaving the force limiter body 150 at the proximal end of the elongated handle housing 120, at least until the slider 146 reaches the distal end of the slot formed in the top of the force limiter body 150. Actuating and/or rotating the lead screw 134 may also (simultaneously and/or sequentially with the actuator member carriage 152) actuate and/or translate the sheath carriage 132 distally to actuate, translate, and/or extend the outer sheath 12 distally and re-sheath and/or cover the coupler 78, the collars 80, the guides 82, and the plurality of actuator members 84 for removal from the patient's anatomy. The medical device system 10 (without the medical device implant 16) may then be removed from the patient's anatomy.

FIG. 14 illustrates an example rotatable collar 256. In at least some embodiments, except as described herein, the rotatable collar 256 may include similar structure and/or may function similarly to the rotatable collar 156 described above. In some embodiments, the rotatable collar 256 may include a proximal portion 280 and a distal portion 282. In some embodiments, the proximal portion 280 may include a plurality of notches at a proximal end of the rotatable collar 256, the plurality of notches being configured to engage with the ring 154, as discussed above with respect to the rotatable collar 156. In some embodiments, the rotatable control knob 122 may be disposed about and/or over the proximal portion 280 of the rotatable collar 256. In some embodiments, a middle portion 283 of the rotatable collar 256 may be disposed and/or extend between the proximal portion 280 and the distal portion 282. In some embodiments, the middle portion 283 may extend radially outward farther than the proximal portion 280 and/or the distal portion 282, and/or may form a radially extending ridge along an outer surface of the rotatable collar 256. The middle portion 283 and/or the radially extending ridge may include a proximal face and a distal face.

Figure 15:
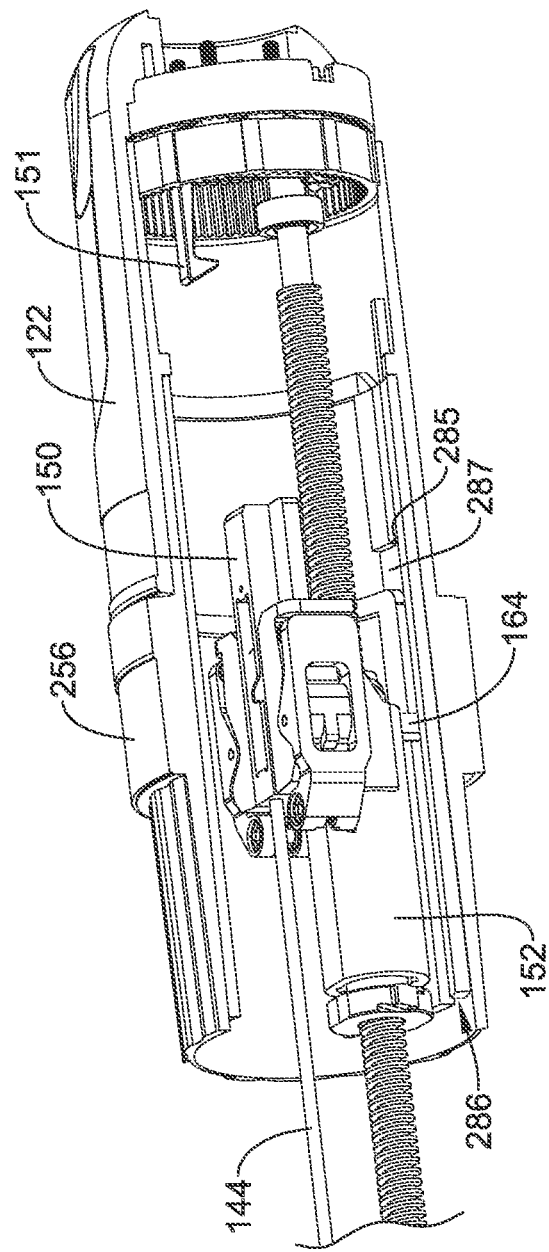
FIGS. 15-18 are cut away views illustrating an example of coordinated movement of some components within the example medical device handle of FIG. 4 using the example collar of FIG. 14.

In some embodiments, the rotatable collar 256 may include one or more slots disposed along an inner surface of the rotatable collar 256. In some embodiments, the rotatable collar 256 may include a first internally-facing longitudinal slot 286 extending less than a full length of the rotatable collar. In some embodiments, the actuator member carriage 152 may include a laterally-extending protrusion or flag member 164 configured to engage with the first internally-facing longitudinal slot 286 (as shown in FIG. 15 for example). In general, the laterally-extending protrusion or flag member 164 may be designed as a feature that can prevent the rotatable collar 256 from being rotated earlier than desired. For example, the laterally-extending protrusion or flag member 164 may be positioned within and may follow the first internally-facing longitudinal slot 286 along the inner surface of the rotatable collar 256, as illustrated in FIG. 15.

In some embodiments, an internally-facing circumferentially-oriented slot 287 operatively connects the first internally-facing longitudinal slot 286 with a second internally-facing longitudinal slot 288. In some embodiments, the first internally-facing longitudinal slot 286 may terminate proximally at a distally-facing wall 285 of the internally-facing circumferentially-oriented slot 287. In other words, the first internally-facing longitudinal slot 286 may extend distally from the internally-facing circumferentially-oriented slot 287 and/or the distally-facing wall 285. In some embodiments, the first internally-facing longitudinal slot 286 may only extend distally from the internally-facing circumferentially-oriented slot 287 and/or the distally-facing wall 285. In some embodiments, the internally-facing circumferentially-oriented slot 287 may extend between the first internally-facing longitudinal slot 286 and the second internally-facing longitudinal slot 288. In some embodiments, the second internally-facing longitudinal slot 288 may extend both proximally and distally from the internally-facing circumferentially-oriented slot 287. In some embodiments, the first internally-facing longitudinal slot 286 and the second internally-facing longitudinal slot 288 may be oriented substantially parallel to a central longitudinal axis of the rotatable collar 256 and/or to each other.

Figure 16:
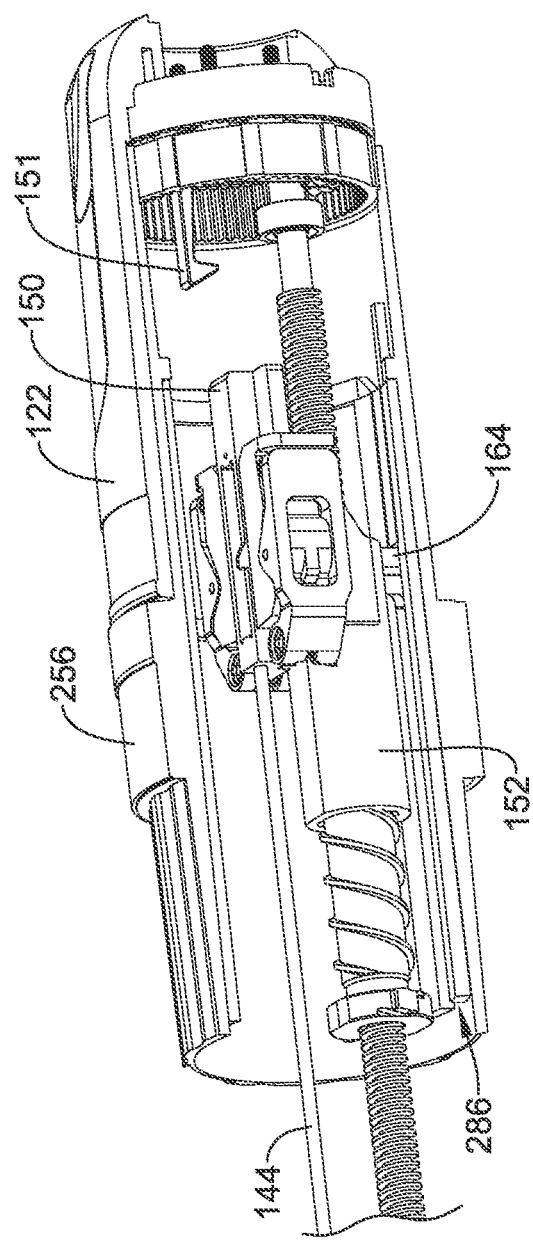

In at least some embodiments, the rotatable collar 256 is prevented from rotating relative to the elongated handle housing 120 when the laterally-extending protrusion or flag member 164 is engaged with and/or positioned within the first internally-facing longitudinal slot 286. In at least some embodiments, the laterally-extending protrusion or flag member 164 is engaged with and/or positioned within the first internally-facing longitudinal slot 286 when the anchor member or braid 70 and/or the medical device implant 16 is in the "delivery" configuration. As seen in FIG. 15 for example, the laterally-extending protrusion or flag member 164 may travel proximally within the first internally-facing longitudinal slot 286 as the rotatable control knob 122 is rotated. Upon reaching the distally-facing wall 285, proximal travel of the laterally-extending protrusion or flag member 164 will be stopped and/or physically prevented by physical interference between the distally-facing wall 285 and the laterally-extending protrusion or flag member 164, as seen in FIG. 16 for example. In other words, the distally-facing wall 285 may form a "hard stop" in the operation of the medical device handle 18.

Upon reaching the distally-facing wall 285 or "hard stop", the user (e.g., physician, etc.) may check the physical placement of the medical device implant 16 using a suitable imaging technique. Also upon reaching the distally-facing wall 285 or "hard stop", the anchor member or braid 70 and/or the medical device implant 16 may be locked into the "deployed" configuration by engagement of the posts 72 with the buckles 76. However, at this point in the procedure, the anchor member or braid 70 and/or the medical device implant 16 may still be reversibly translated toward the "delivery" configuration. The distally-facing wall 285 or "hard stop" may serve as an indication for the user to verify proper positioning of the medical device implant 16. If the medical device implant 16 is not satisfactorily positioned at the target site, the rotatable control knob 122 may be rotated in a second, opposite direction to translate and/or actuate the anchor member or braid 70 and/or the medical device implant 16 back toward the "delivery" configuration for repositioning or withdrawal from the patient. If the medical device implant 16 is satisfactorily positioned at the target site, the user may choose to continue the procedure.

Figure 17:
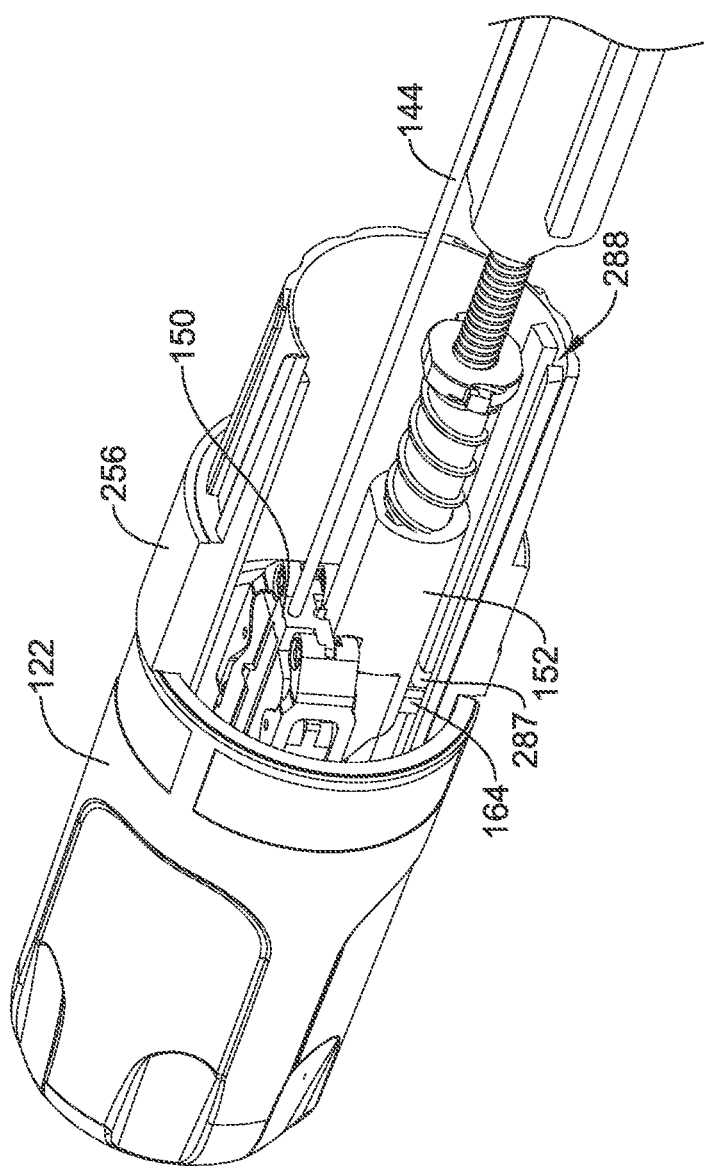
Figure 18:
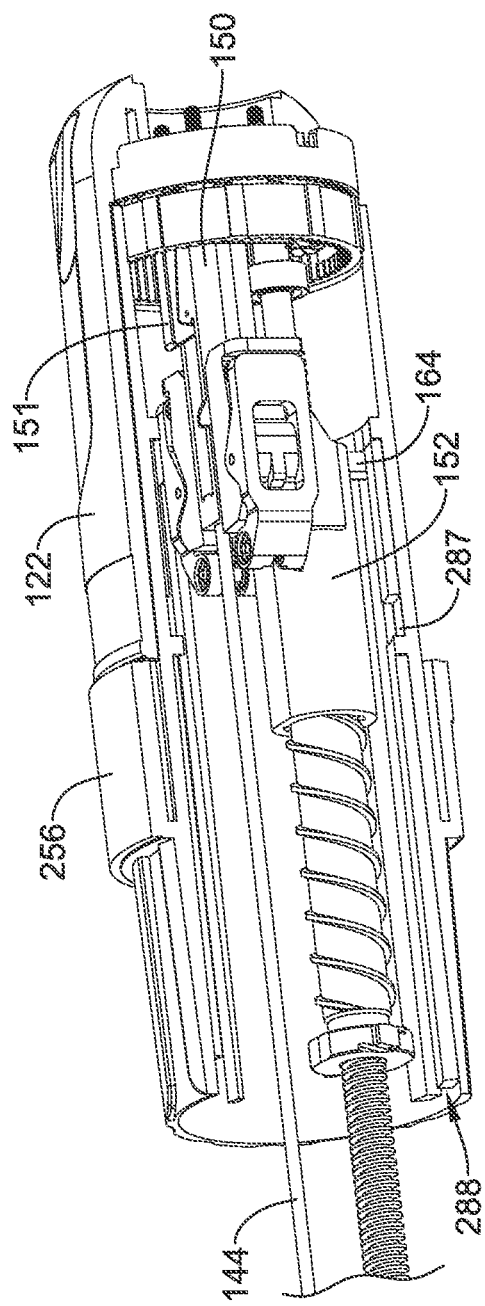

To continue the procedure, the rotatable collar 256 may be rotated about the elongated handle housing 120, thereby engaging the laterally-extending protrusion or flag member 164 with the internally-facing circumferentially-oriented slot 287. In some embodiments, the laterally-extending protrusion or flag member 164 may be engaged with the internally-facing circumferentially-oriented slot 287 when the anchor member or braid 70 and/or the medical device implant 16 is in the "deployed" configuration. The rotatable collar 256 may be rotated about the elongated handle housing 120 to circumferentially translate the laterally-extending protrusion or flag member 164, which remains fixed relative to the elongated handle housing 120, from the first internally-facing longitudinal slot 286 to the second internally-facing longitudinal slot 288, as seen in FIG. 17 for example. After rotating the rotatable collar 256 as described above, and aligning and/or engaging the laterally-extending protrusion or flag member 164 with the second internally-facing longitudinal slot 288, further rotating the rotatable control knob 122 about the elongated handle housing 120 may actuate and/or translate the actuator member carriage 152 and/or the force limiter body 150 proximally within the elongated handle housing 120, thereby retracting the plurality of actuator members 84 from the plurality of locking mechanisms (e.g., separating the plurality of actuator members 84 from the buckles 76) and/or the medical device implant 16 to release the medical device implant 16 at the target site in the "released" configuration. When the actuator member carriage 152 and/or the force limiter body 150 is retracted within the elongated handle housing 120, the force limiter body 150 engages a retainer clip 151 fixed to a proximal end of the elongated handle housing 120, as seen in FIG. 18. Engaging the force limiter body 150 with the retainer clip 151 prevents the force limiter body 150 and/or the plurality of actuator members 84 (via the second shaft or hypotube 144) from being actuated, translated, and/or re-extended distally. In some embodiments, the laterally-extending protrusion or flag member 164 may be engaged with a proximal portion of the second internally-facing longitudinal slot 288 when the anchor member or braid 70 and/or the medical device implant 16 is in the "released" configuration.

After releasing the medical device implant 16 and engaging the force limiter body 150 with the retainer clip 151, the rotatable control knob 122 may be rotated in the second, opposite direction to actuate and/or rotate the lead screw 134. Actuating and/or rotating the lead screw 134 may actuate and/or translate the actuator member carriage 152 and the laterally-extending protrusion of flag member 164 distally within the second internally-facing longitudinal slot 288, while leaving the force limiter body 150 attached to the retainer clip 151 at the proximal end of the elongated handle housing 120. Actuating and/or rotating the lead screw 134 may also (simultaneously and/or sequentially with the actuator member carriage 152) actuate and/or translate the sheath carriage 132 distally to actuate, translate, and/or extend the outer sheath 12 distally and re-sheath and/or cover the coupler 78, the collars 80, the guides 82, and the plurality of actuator members 84 for removal from the patient's anatomy. The medical device system 10 (without the medical device implant 16) may then be removed from the patient's anatomy.

Figure 19:
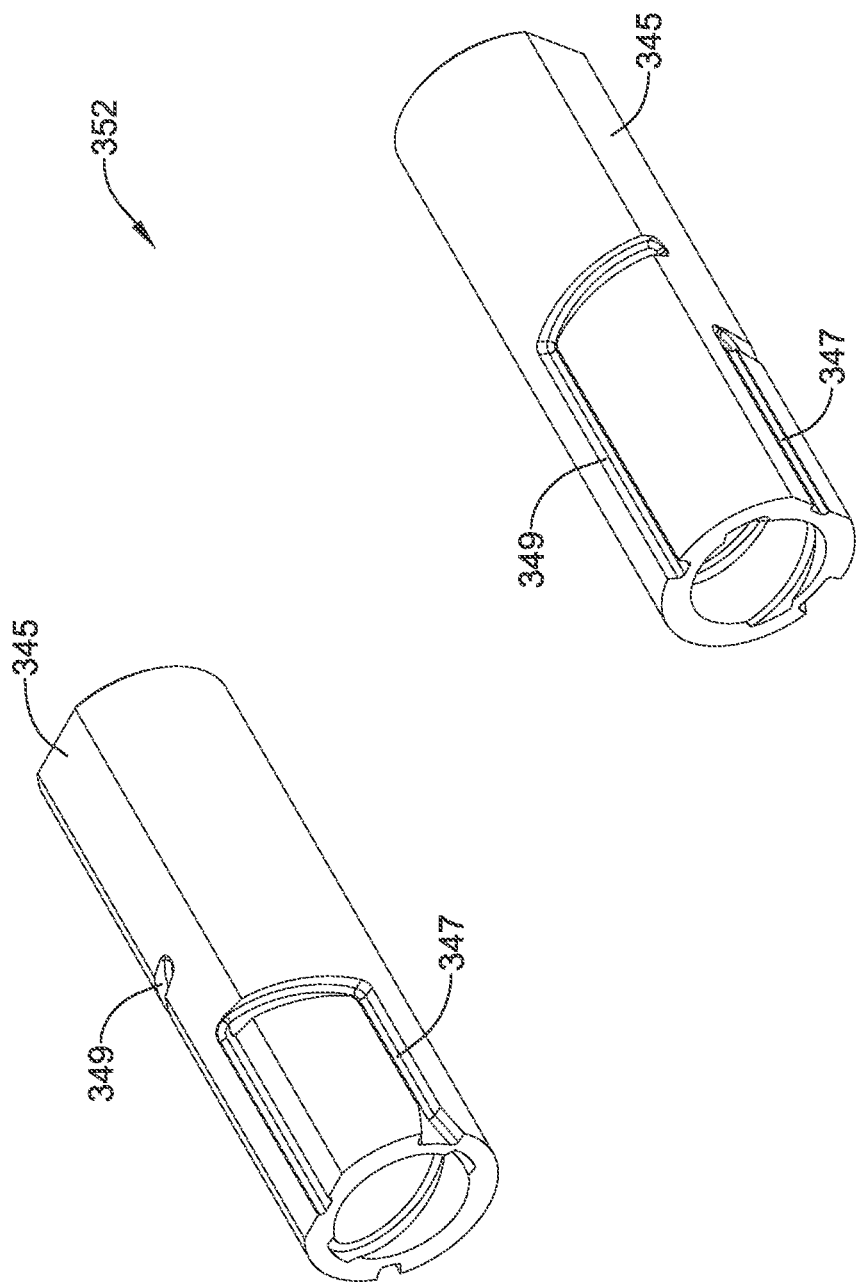
FIG. 19 illustrates an example actuator member carriage of the example medical device handle of FIG. 4.

FIG. 19 illustrates an example actuator member carriage 352. In at least some embodiments, except as described herein, the actuator member carriage 152 may include similar structure and/or may function similarly to the actuator member carriage 152 described above. In some embodiments, the actuator member carriage 352 may include a flattened portion 345 along an exterior surface thereof. In some embodiments, the actuator member carriage 352 may include a plurality of tracks (e.g., grooves, slots, etc.) formed in the exterior surface of the actuator member carriage 352. In some embodiments, the plurality of tracks may include a first track 347 and a second track 349 formed in the exterior surface of the actuator member carriage 352. In at least some embodiments, the first track 347 and the second track 349 may be distinct from and/or independent of each other.

In some embodiments, the first track 347 may have a first end and a second end each opening toward and/or at a proximal end of the actuator member carriage 352. In some embodiments, the first track 347 may include a first longitudinally-extending leg extending distally from the first end of the first track 347 and/or the proximal end of the actuator member carriage 352. In some embodiments, the first track 347 may include a second longitudinally-extending leg extending distally from the second end of the first track 347 and/or the proximal end of the actuator member carriage 352. In some embodiments, the first longitudinally-extending leg and the second longitudinally-extending leg may be joined together by a generally transversely extending leg to form a continuous groove in the exterior surface of the actuator member carriage 352 from the first end of the first track 347 to the second end of the first track 347. As such, the first track 347 may have a generally U-shaped configuration opening toward the proximal end of the actuator member carriage 352. In some embodiments, the second end of the first track 347 may be disposed within and/or along the flattened portion 345 of the exterior surface of the actuator member carriage 352 at the proximal end of the actuator member carriage 352.

In some embodiments, the second track 349 may include a first end and a second end. In some embodiments, the first end of the second track 349 may open toward and/or be disposed within the flattened portion 345 of the exterior surface of the actuator member carriage 352 at or near a middle portion of the actuator member carriage 352. In at least some embodiments, the first end of the second track 349 may be disposed distally of the first track 347. In some embodiments, the second end of the second track 349 may open toward and/or at the proximal end of the actuator member carriage 352. In some embodiments, the second track 349 may form a generally reverse L-shaped configuration, with a generally transversely-extending leg at and/or adjacent the first end of the second track 349 and a longitudinally-extending leg extending distally from the second end of the second track 349 and/or the proximal end of the actuator member carriage 352 to the generally transversely-extending leg. In at least some embodiments, the generally transversely-extending leg may be curved and/or angled from the first end of the second track 349 toward the proximal end of the actuator member carriage 352.

Figure 20:
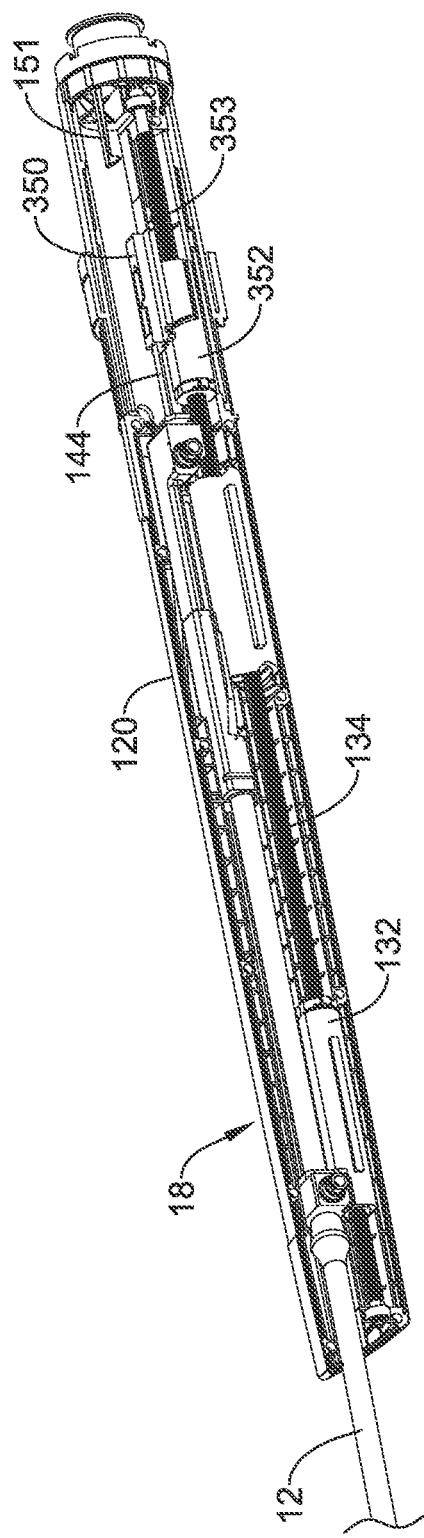
FIGS. 20-24 are cut away views illustrating an example of coordinated movement of some components within the example medical device handle of FIG. 4 using the example actuator member carriage of FIG. 19.
Figure 21:
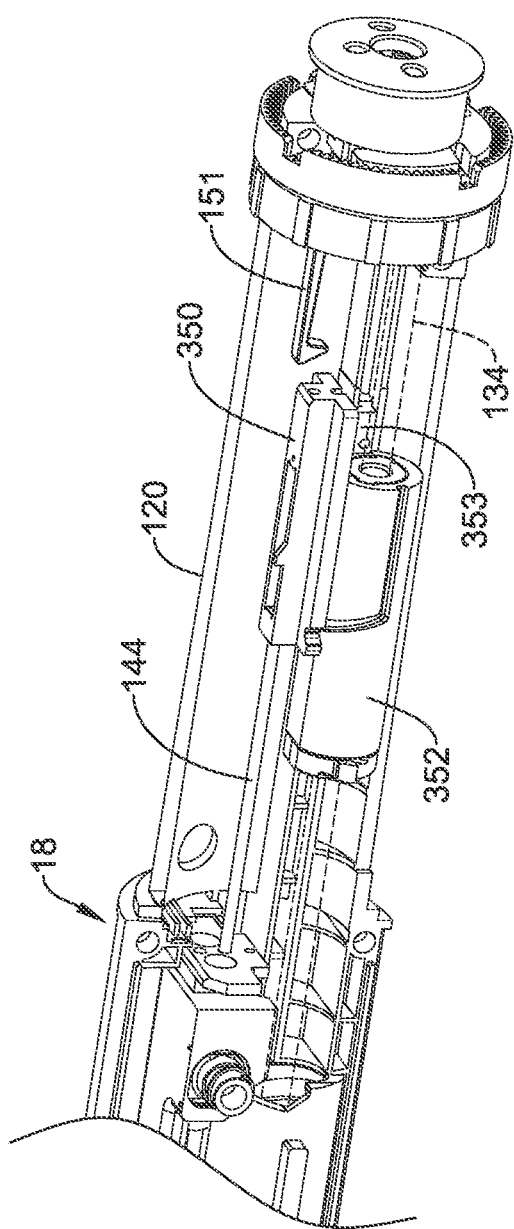

In some embodiments, the medical device handle 18 may include the actuator member carriage 352 similar to the actuator member carriage 152 above. In some embodiments, the medical device handle 18 may include a force limiter body 350, wherein a bottom surface of the force limiter body 350 may be configured to engage the flattened portion 345 of the actuator member carriage 352, as seen in FIGS. 20 and 21 for example. In some embodiments, the force limiter body 350 may include a laterally-extending pin (not shown) extending from the bottom surface and configured to engage with and/or extend into the first end of the second track 349.

In use, as the rotatable control knob 122 is rotated and the lead screw 134 turns, the actuator member carriage 352 is translated proximally similar to the actuator member carriage 352 above. The force limiter body 350, being engaged with the actuator member carriage 352 via the laterally-extending pin and the second track 349, also translates proximally within the elongated handle housing 120. Disposed along an interior surface of the elongated handle housing 120 may be a cam block 353, as seen in FIG. 21. In at least some embodiments, the cam block 353 may include a pin member extending inwardly from and/or relative to the elongated handle housing 120. In some embodiments, the cam block 353 and/or the pin member thereof may engage with the first end of the first track 347. As the actuator member carriage 352 is translated proximally, the cam block 353 advances along the first longitudinally-extending leg of the first track 347 toward the generally transversely extending leg of the first track 347 and the force limiter body 350 simultaneously translates proximally, thereby actuating the anchor member or braid 70 and/or the medical device implant 16 from the "delivery" configuration toward the "deployed" configuration.

When the cam block 353 reaches the generally transversely extending leg of the first track 347, the user may experience tactile feedback (e.g., additional force required to rotate the rotatable control knob 122, for example). At this point, the plurality of locking mechanisms may be fully engaged (e.g., the posts 72 may be engaged with the buckles 76), and/or the anchor member or braid 70 and/or the medical device implant 16 may be disposed in the "deployed" configuration.

Figure 22:
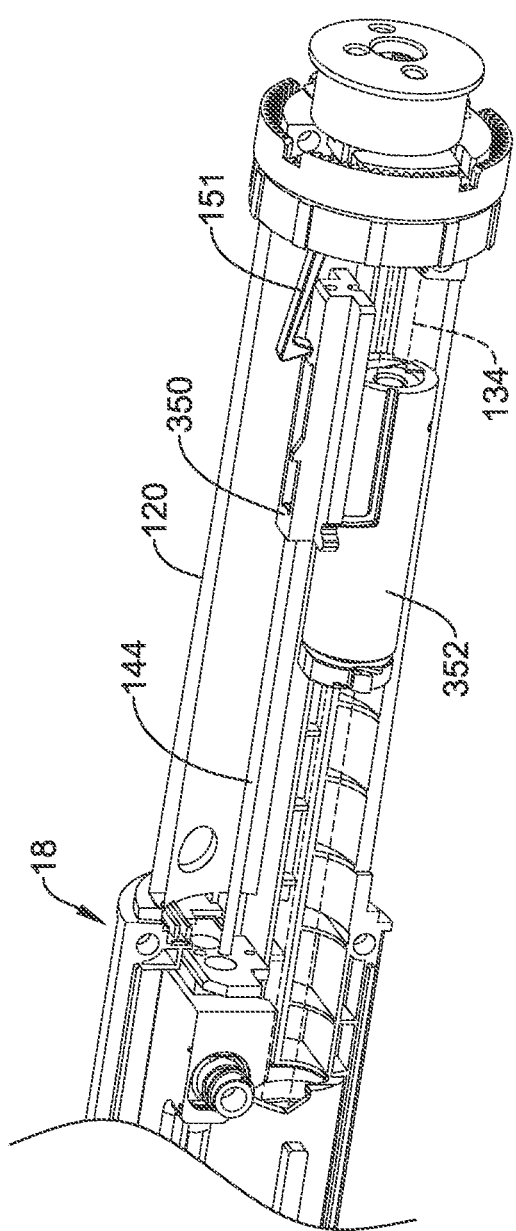
Figure 23:
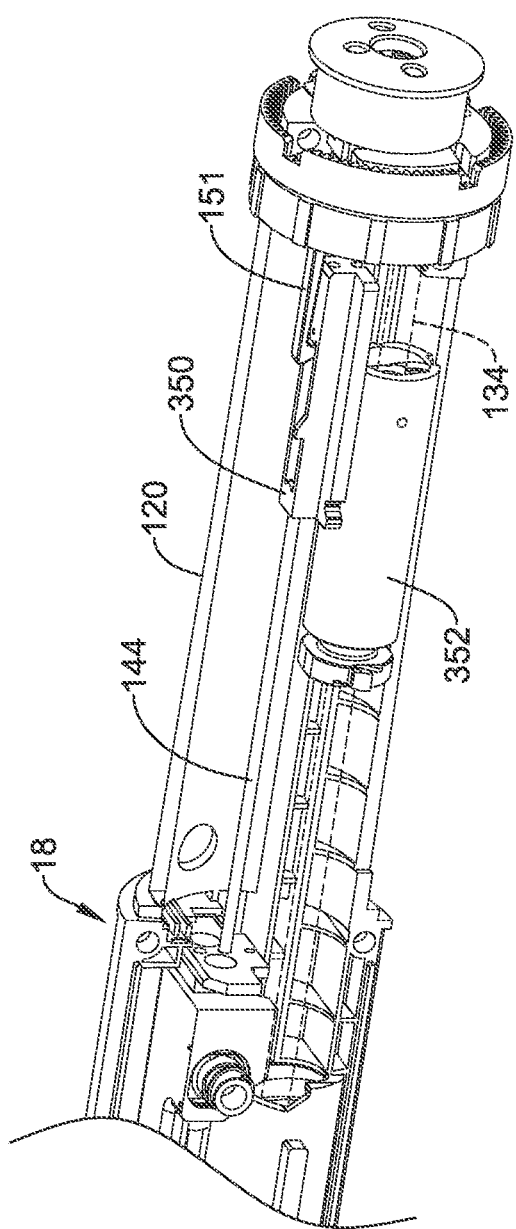

Further rotation of the rotatable control knob 122 and/or translation of the actuator member carriage 352 results in rotation of the actuator member carriage 352 as the generally transversely extending leg engages with the pin member of the cam block 353, as seen in FIG. 22. In some embodiments, the actuator member carriage 352 remains generally axially fixed as the actuator member carriage 352 rotates (e.g., does not translate proximally or distally). At the same time, since the actuator member carriage 352 is rotating about the lead screw 134, the laterally-extending pin of the force limiter body 350 advances along the generally transversely-extending leg of the second track 349. In at least some embodiments, due to the aforementioned curved and/or angled configuration of the generally transversely-extending leg of the second track 349, the laterally-extending pin advances proximally within the second track 349 and thus the force limiter body 350 may be further retracted proximally as the laterally-extending pin advances along the second track 349 while the actuator member carriage 352 is rotated, thereby withdrawing the plurality of actuator members 84 from the plurality of locking mechanisms and/or the medical device implant 16, until the force limiter body 350 engages with the retainer clip 151 fixed to the proximal end of the elongated handle housing 120, as seen in FIG. 23. Once the force limiter body 350 engages with the retainer clip 151, the medical device implant is disposed in the "released" configuration.

Figure 24:
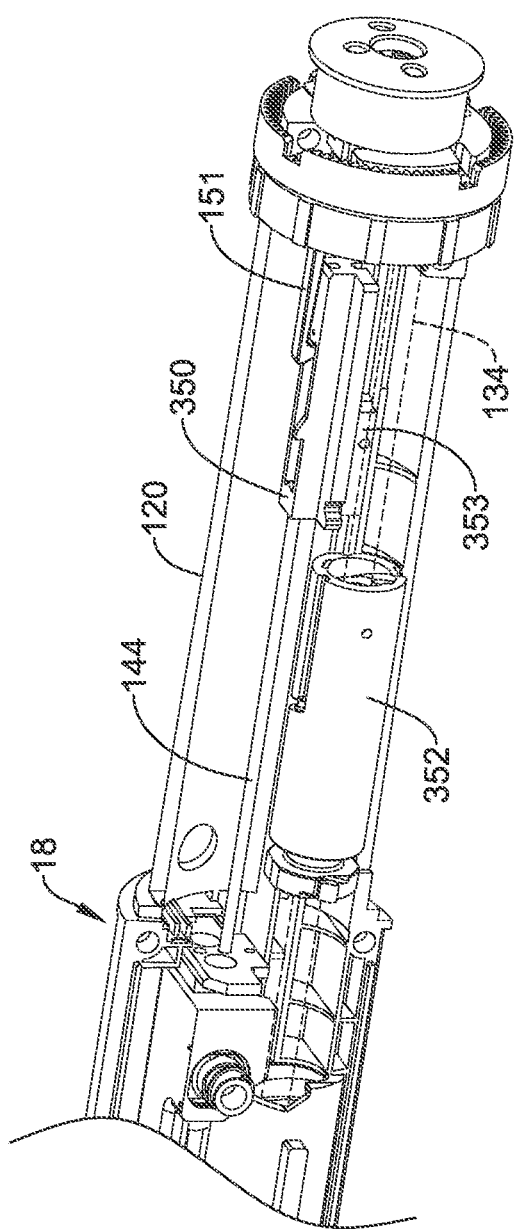

After engaging the force limiter body 350 with the retainer clip 151, the rotatable control knob 122 may be rotated in a second, opposite direction, thereby actuating the lead screw 134 and translating the sheath carriage 132 and/or the actuator member carriage 352 distally within the elongated handle housing 120. As seen in FIG. 24, as the actuator member carriage 352 translates distally, the laterally-extending pin advances along the longitudinally-extending leg of the second track 349 toward the second end of the second track 349 and/or the proximal end of the actuator member carriage 352. At the same time, the pin member and/or the cam block advances along the second longitudinally-extending leg of the first track 347 toward the second end of the first track 347 and/or the proximal end of the actuator member carriage 352. The force limiter body 350 may remain engaged with the retainer clip 151 and thus, stationary with respect to the elongated handle housing 120.

Similar to the discussion above, actuating and/or rotating the lead screw 134 may also (simultaneously and/or sequentially with the actuator member carriage 352) actuate and/or translate the sheath carriage 132 distally to actuate, translate, and/or extend the outer sheath 12 distally and re-sheath and/or cover the coupler 78, the collars 80, the guides 82, and the plurality of actuator members 84 for removal from the patient's anatomy. The medical device system 10 (without the medical device implant 16) may then be removed from the patient's anatomy.

In some embodiments, a method of deploying a medical device implant may comprise advancing a medical device system to a treatment location, the medical device system including an elongated handle housing having a proximal end, a distal end, and a longitudinal axis extending from the proximal end to the distal end a rotatable collar disposed about the proximal end of the elongated handle housing, and a rotatable control knob disposed about a proximal portion of the rotatable collar. The rotatable collar may include a first internally-facing longitudinal slot extending less than a full length of the rotatable collar. In some embodiments, the first internally-facing longitudinal slot may terminate proximally at a distally-facing wall of an internally-facing circumferentially-oriented slot. The rotatable control knob may be configured to actuate a percutaneous medical device disposed within a distal end of a delivery sheath coupled to the elongated handle housing between a delivery configuration, a deployed configuration, and a released configuration. The method may comprise rotating the rotatable control knob in a first direction to axially translate a carriage element disposed within the elongated handle housing proximally along the first internally-facing longitudinal slot from the delivery configuration to the deployed configuration, the carriage element including a laterally-extending protrusion engaged with the first internally-facing longitudinal slot. The method may comprise rotating the rotatable collar about the elongated handle housing to circumferentially translate the laterally-extending protrusion relative to the rotatable collar along the internally-facing circumferentially-oriented slot from the first internally-facing longitudinal slot to a second internally-facing longitudinal slot. The method may comprise rotating the rotatable control knob in the first direction to axially translate the carriage element proximally along the second internally-facing longitudinal slot from the deployed configuration to the released configuration, wherein the medical device is released from an attachment element at the treatment location.

In some embodiments, the method may further include: after releasing the medical device at the treatment location, rotating the rotatable control knob in a second direction opposite the first direction to axially translate at least a portion of the carriage element distally along the second internally-facing longitudinal slot to re-sheath the attachment element.

In some embodiments, the elongated handle housing may include a release ring engaged with the rotatable collar that is axially translatable from a first position to a second position, the release ring including an arm extending within the rotatable collar. In some embodiments, the arm may prevent the laterally-extending protrusion from accessing the internally-facing circumferentially-oriented slot from the first internally-facing longitudinal slot when the release ring is in the first position.

In some embodiments, the method may further include: after rotating the rotatable control knob in a first direction to axially translate a carriage element disposed within the elongated handle housing proximally along the first internally-facing longitudinal slot from the delivery configuration to the deployed configuration, the release ring may be translated proximally relative to the rotatable collar to shift the release ring from the first position to the second position, thereby permitting the laterally-extending protrusion to access the internally-facing circumferentially-oriented slot from the first internally-facing longitudinal slot.

In some embodiments, the method may include additional and/or different steps commensurate with the disclosure. For example, certain features may be omitted or modified as disclosed herein, and steps related to those omitted or modified features may be similarly omitted or modified. Additionally, new and/or additional steps may be taken with respect to the omitted or modified features in accordance with the disclosure.

The materials that can be used for the various components of the medical device system 10 (and/or other systems disclosed herein) and the various tubular members disclosed herein may include those commonly associated with medical devices. For simplicity purposes, the following discussion makes reference to the outer sheath 12 and/or the inner catheter 14. However, this is not intended to limit the devices and methods described herein, as the discussion may be applied to other similar tubular members and/or components of tubular members or devices disclosed herein.

The outer sheath 12, the inner catheter 14, and/or the tubular anchor member or braid 70, may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the outer sheath 12 and the inner catheter 14 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the medical device system 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device system 10 to achieve the same result.

In some embodiments, a degree of Magnetic Resonance Imaging (MRI) compatibility is imparted into the medical device system 10. For example, the outer sheath 12, the inner catheter 14, and/or the tubular anchor member or braid 70, or portions thereof, may be made of a material that does not substantially distort the image and create substantial artifacts (i.e., gaps in the image). Certain ferromagnetic materials, for example, may not be suitable because they may create artifacts in an MRI image. The outer sheath 12 and the inner catheter 14, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

A sheath or covering (not shown) may be disposed over portions or all of the outer sheath 12 and the inner catheter 14 that may define a generally smooth outer surface for the medical device system 10. In other embodiments, however, such a sheath or covering may be absent from a portion of all of the medical device system 10, such that the outer sheath 12 and the inner catheter 14 may form an outer surface. The sheath may be made from a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the exterior surface of the medical device system 10 (including, for example, the exterior surface of the outer sheath 12 and the inner catheter 14) may be sandblasted, beadblasted, sodium bicarbonate-blasted, electropolished, etc. In these as well as in some other embodiments, a coating, for example a lubricious, a hydrophilic, a protective, or other type of coating may be applied over portions or all of the sheath, or in embodiments without a sheath over portion of the outer sheath 12 and the inner catheter 14, or other portions of the medical device system 10. Alternatively, the sheath may comprise a lubricious, hydrophilic, protective, or other type of coating. Hydrophobic coatings such as fluoropolymers provide a dry lubricity which improves device handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Other suitable coatings are also contemplated.

The coating and/or sheath may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A medical device handle for percutaneous delivery of a medical device implant, comprising:
   an elongated handle housing having a proximal end, a distal end, and a longitudinal axis extending from the proximal end to the distal end;
   a rotatable collar disposed about the proximal end of the elongated handle housing; and
   a rotatable control knob disposed about a proximal portion of the rotatable collar;
   wherein the rotatable collar includes a first internally-facing longitudinal slot extending less than a full length of the rotatable collar and terminating proximally at a distally-facing wall of an internally-facing circumferentially-oriented slot;

wherein the rotatable control knob is configured to actuate the medical device implant between a delivery configuration, a deployed configuration, and a released configuration.

2. The medical device handle of claim 1, wherein the medical device implant is reversibly actuatable between the delivery configuration and the deployed configuration.

3. The medical device handle of claim 1, wherein the internally-facing circumferentially-oriented slot operatively connects the first internally-facing longitudinal slot with a second internally-facing longitudinal slot extending both proximally and distally from the internally-facing circumferentially-oriented slot.

4. The medical device handle of claim 3, wherein the elongated handle housing includes an axial translation mechanism disposed therein and operatively connected to the rotatable control knob.

5. The medical device handle of claim 4, wherein the axial translation mechanism converts rotational motion of the rotatable control knob into axial translation of a carriage element disposed within the elongated handle housing.

6. The medical device handle of claim 5, wherein the elongated handle housing includes a locking clip configured to engage an opening in the carriage element when the carriage element is axially translated to its proximalmost position, the locking clip preventing distal translation of at least a portion of the carriage element after engaging the opening in the carriage element.

7. The medical device handle of claim 5, wherein the carriage element includes a laterally-extending protrusion configured to engage with the rotatable collar.

8. The medical device handle of claim 7, wherein the rotatable collar is prevented from rotating when the laterally-extending protrusion is engaged with the first internally-facing longitudinal slot.

9. The medical device handle of claim 7, wherein the laterally-extending protrusion is engaged with a distal portion of the first internally-facing longitudinal slot when the medical device implant is in the delivery configuration.

10. The medical device handle of claim 7, wherein the laterally-extending protrusion is engaged with the internally-facing circumferentially-oriented slot when the medical device implant is in the deployed configuration.

11. The medical device handle of claim 7, wherein the laterally-extending protrusion is engaged with a proximal portion of the second internally-facing longitudinal slot when the medical device implant is in the released configuration.

12. The medical device handle of claim 7, further including a release ring engaged with the rotatable collar that is axially translatable from a first position to a second position, the release ring including an arm extending within the rotatable collar.

13. The medical device handle of claim 12, wherein the arm prevents the laterally-extending protrusion from accessing the internally-facing circumferentially-oriented slot from the first internally-facing longitudinal slot when the release ring is in the first position.

14. The medical device handle of claim 12, wherein a plurality of compression springs biases the release ring distally relative to the rotatable collar.

15. The medical device handle of claim 12, wherein proximal translation of the release ring relative to the rotatable collar shifts the release ring from the first position to the second position, thereby permitting the laterally-extending protrusion to access the internally-facing circumferentially-oriented slot from the first internally-facing longitudinal slot.

* * * * *